United States Patent
Saini

(10) Patent No.: US 10,624,791 B2
(45) Date of Patent: Apr. 21, 2020

(54) ARTIFICIAL VISION INTRAOCULAR IMPLANT DEVICE

(71) Applicant: Manjinder Saini, Germantown, TN (US)

(72) Inventor: Manjinder Saini, Germantown, TN (US)

(*) Notice: Subject to any disclaimer, the term of this patent is extended or adjusted under 35 U.S.C. 154(b) by 331 days.

(21) Appl. No.: 15/812,433

(22) Filed: Nov. 14, 2017

(65) Prior Publication Data

US 2018/0353332 A1 Dec. 13, 2018

Related U.S. Application Data

(60) Provisional application No. 62/517,894, filed on Jun. 10, 2017.

(51) Int. Cl.
*A61F 9/08* (2006.01)
*A61F 2/16* (2006.01)

(52) U.S. Cl.
CPC .............. *A61F 9/08* (2013.01); *A61F 2/1624* (2013.01); *A61F 2250/0002* (2013.01)

(58) Field of Classification Search
CPC ........ A61F 9/08; A61F 2/1648; A61F 2/1613; A61F 2250/0001; A61F 2250/0002; A61F 2250/0091; G02B 2027/014; G02B 2207/114; G02B 2207/117; G02B 2207/125; G02B 2207/129
See application file for complete search history.

(56) References Cited

U.S. PATENT DOCUMENTS

| 5,653,751 | A | * | 8/1997 | Samiy | A61F 2/16 128/899 |
| 5,935,155 | A | * | 8/1999 | Humayun | A61M 5/3213 607/54 |
| 6,972,032 | B2 | * | 12/2005 | Aharoni | A61F 2/1613 623/6.15 |
| 7,001,427 | B2 | * | 2/2006 | Aharoni | A61F 9/08 623/4.1 |
| 8,197,539 | B2 | * | 6/2012 | Nasiatka | A61F 9/08 607/54 |

(Continued)

FOREIGN PATENT DOCUMENTS

WO WO-2006015315 A2 * 2/2006 ............... A61F 9/08

*Primary Examiner* — Paul B Prebilic
(74) *Attorney, Agent, or Firm* — Waller Lansden Dortch & Davis, LLP; Matthew C. Cox

(57) ABSTRACT

An intraocular implant device for restoring, augmenting, or improving vision of a user, the implant including an intraocular implant body shaped for positioning inside a lens chamber of an eye, the body having an anterior side facing the cornea of the eye, and a posterior side facing the retina of the eye; a photoelectric sensor disposed on the anterior side of the body; wherein the photoelectric sensor is operable to receive incident light through the cornea and to convert the received light into electrical energy for use with one or more circuit components disposed on the body, and wherein the photoelectric sensor is nearly simultaneously operable to convert the received light into image data. The ocular implant device may include a projector for projecting the image data onto the retina of a user. The ocular implant may include a wireless receiver for receiving image data transmissions from an external source.

11 Claims, 24 Drawing Sheets

(56) References Cited

U.S. PATENT DOCUMENTS

| | | | |
|---|---|---|---|
| 2011/0002464 A1* | 1/2011 | Lipshitz | A61F 2/14 |
| | | | 380/270 |
| 2013/0250078 A1* | 9/2013 | Levy | A61F 9/08 |
| | | | 348/62 |
| 2018/0353332 A1* | 12/2018 | Saini | A61F 9/08 |

* cited by examiner

ARTIFICIAL VISION INTRAOCULAR IMPLANT DEVICE

CROSS-REFERENCES TO RELATED APPLICATIONS

This application claims priority to and benefit of U.S. Provisional Application No. 62/517,894 filed Jun. 10, 2017 entitled INTRAOCULAR IMPLANT DEVICE, which is herein incorporated by reference in its entirety.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND

The present disclosure relates generally to ophthalmologic devices for implantation into the eye, and more particularly to intraocular implant devices and associated power supplies for enhancing or restoring vision in humans and animals.

Many people experience impaired vision as a result of corneal dysfunction or damage, lens dysfunction or damage, or other conditions of the eye that lead to inability of light to properly pass through the eye to the retina. Various medical procedures have been developed to attempt to correct these types of problems to improve or to restore vision. For example, lens replacement procedures are often used to remove a damaged or occluded lens from the eye. An artificial intraocular lens implant may be inserted into the eye through a small incision in the cornea during a surgical procedure to replace the removed lens. Such procedures are helpful to improve conditions such as cataracts or occluded lenses.

However, such conventional procedures for replacing occluded or damaged lenses with replacement intraocular lens implants are often inadequate to restore or enhance vision of patients with corneal conditions. As light initially enters the eye through the cornea, any conditions of the cornea which scatter or block light are generally not amenable to treatment via artificial lens replacement procedures. Although many corneal replacement procedures do exist, they are often inadequate in improving or restoring sight. Additionally, such procedures require extensive healing times and may cause other complications in the eye.

What is needed are improvements in devices and methods for improving or restoring vision in patients with impaired cornea or lens tissue in the eye.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One aspect of the present disclosure provides an intraocular photoelectric power supply system (IO-PEPS) for providing power to one or more microelectronic devices implanted into a human or animal eye. The intraocular photoelectric power supply system provides an implant shaped and sized to fit inside the intraocular lens chamber after a natural lens has been removed. The implant device of the intraocular photoelectric power supply system may be inserted into the lens chamber through a small hole in the cornea utilizing conventional lens replacement surgical tools and techniques. The implant device includes one or more photo-sensors, such as but not limited to a photoelectric device configured to convert incident light into electricity, such as a photovoltaic cell. The photo-sensor or photo-sensor array is positioned on the anterior side of the implant device such that light passing through the cornea will be incident on the sensor or sensor array when the implant device is housed in the lens chamber of the eye. The incoming light irradiating the sensor or sensor array is converted to electricity, and is thus available for use by other electronics included on the implant device or otherwise installed within the eye. The incoming light may be specifically tuned to a desired frequency, wavelength, quantity, etc. for optimized power generation using the photoelectric device. The generated electricity may be used immediately, or may be stored in a power storage medium such as a battery on the implant or in the eye for later use.

Another aspect of the present disclosure includes an intraocular projection device configured for implantation into an intraocular cavity formed in the lens chamber after a natural lens is removed. The projector implant device, or artificial projector lens implant, includes an implant having an anterior side oriented toward the cornea and a posterior side oriented toward the retina. An optical light emitter, or projector, is installed on the posterior side of the implant facing back into the eye toward the retina. The projector is operable to emit light from the implant located in the lens chamber through the eye toward the retina, thereby forming a desired light pattern on the retina. The emitted light pattern from the projector corresponds to an image to be processed by the user's brain, and may simulate a natural light array associated with a real or artificial image. The projector implant device is miniaturized such that the projector is compact enough to fit on a normal-sized lens implant in the intraocular lens chamber after removal of the natural lens of the eye.

In some embodiments, the implant includes both a projector and a photoelectric device of an intraocular photoelectric power supply to provide electrical power for the projector. The projector is positioned on the posterior side of the lens implant facing the retina, and the photoelectric array is positioned on the anterior side of the implant facing the cornea. Natural or artificial light entering the cornea is incident on the photoelectric array on the anterior side of the implant inside the lens chamber, and the electrical power generated by the photoelectric array is transferred to the projector located on the posterior side of the implant facing the retina. The generated electrical power is used to power the projector to emit photons in a light pattern corresponding to a desired image onto the retina.

Yet another aspect of the present disclosure provides an intraocular implant device configured for implantation into the lens chamber after removal of a natural lens. The intraocular lens implant device includes a projector on the posterior side facing toward the retina, a photoelectric array on the anterior side facing toward the cornea, and an external light source spaced from the eye configured to irradiate a beam of light through the cornea onto the photoelectric array. The light from the light source is tuned to provide optimal photoelectric conversion into electricity using the specific photoelectric material installed on the implant. The external light source may be operated with an intensity much higher than natural light because the light from the light source is not incident on the retina, but is rather blocked by the artificial intraocular lens implant and used for photoelectric generation of electric power for use by microelectronics within the eye such as but not limited to the projector on the intraocular implant device.

Numerous other objects, advantages and features of the present disclosure will be readily apparent to those of skill in the art upon a review of the following drawings and description of a preferred embodiment.

DETAILED DESCRIPTION

Figure 1:
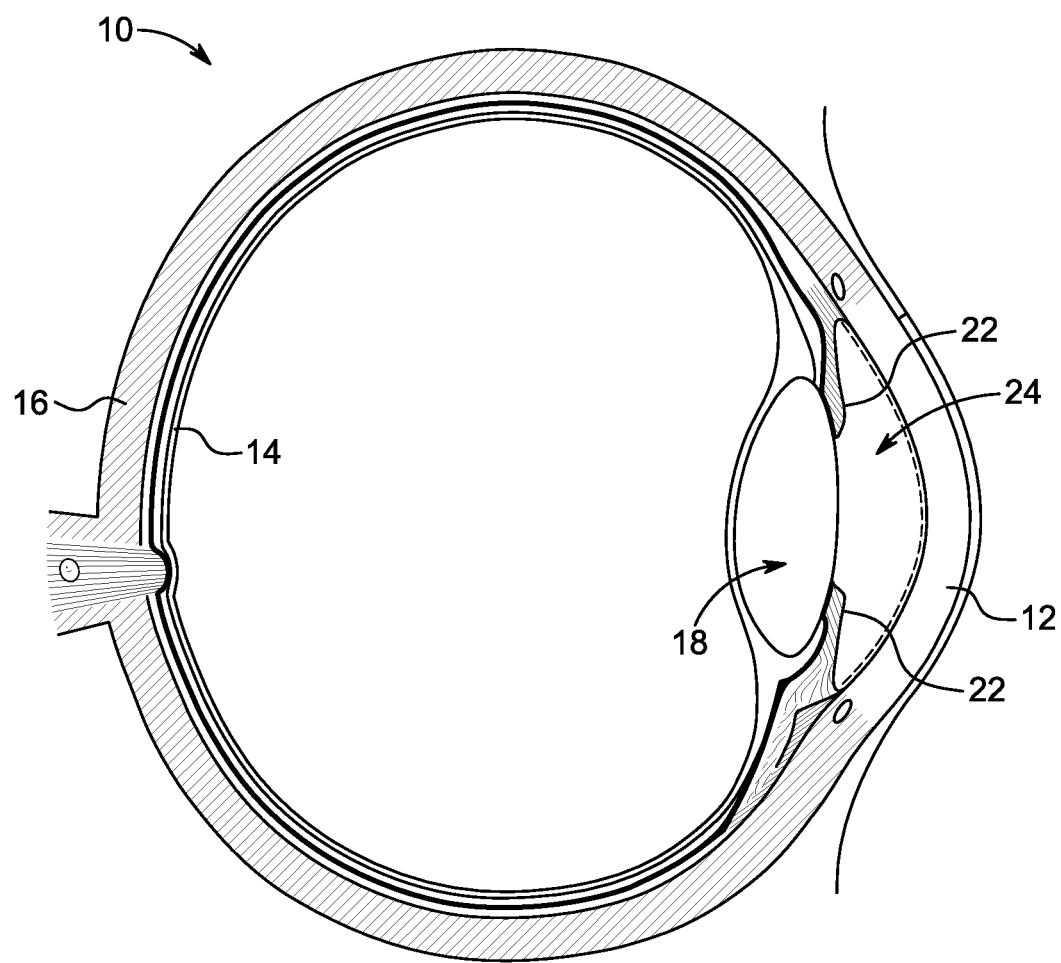
FIG. 1 is a schematic view of an embodiment of an eye with an open lens chamber having a natural lens removed.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention. Those of ordinary skill in the art will recognize numerous equivalents to the specific apparatus and methods described herein. Such equivalents are considered to be within the scope of this invention and are covered by the claims.

In the drawings, not all reference numbers are included in each drawing, for the sake of clarity. In addition, positional terms such as "upper," "lower," "side," "top," "bottom," etc. refer to the apparatus when in the orientation shown in the drawing, or as otherwise described. A person of skill in the art will recognize that the apparatus can assume different orientations when in use.

Referring now to the drawings, FIG. 1 illustrates an example schematic of an eye 10, showing a cornea 12 through which light initially enters the eye. Eye 10 includes a retina 14 on the opposite side of the eye positioned to receive the incoming light. The sclera 16 surrounds the exterior of the eye 10. A lens is typically positioned in lens chamber 18. The iris 22 provides an opening allowing light to pass from the anterior chamber 24 into the lens chamber 18. Many conventional procedures are currently known for removal of a damaged or occluded lens from lens chamber 18. For example, in cataract surgery a damaged lens may be phaco-emulsified using a tool to break up the lens. The broken-up lens may then be aspirated from the eye using a negative pressure, and replaced with a liquid solution to maintain the form of the empty lens chamber 18. Following such procedures, an artificial intraocular lens implant is inserted into the empty lens chamber 18 using known tools and techniques. Such implant procedures are easily reversed.

Figure 2:
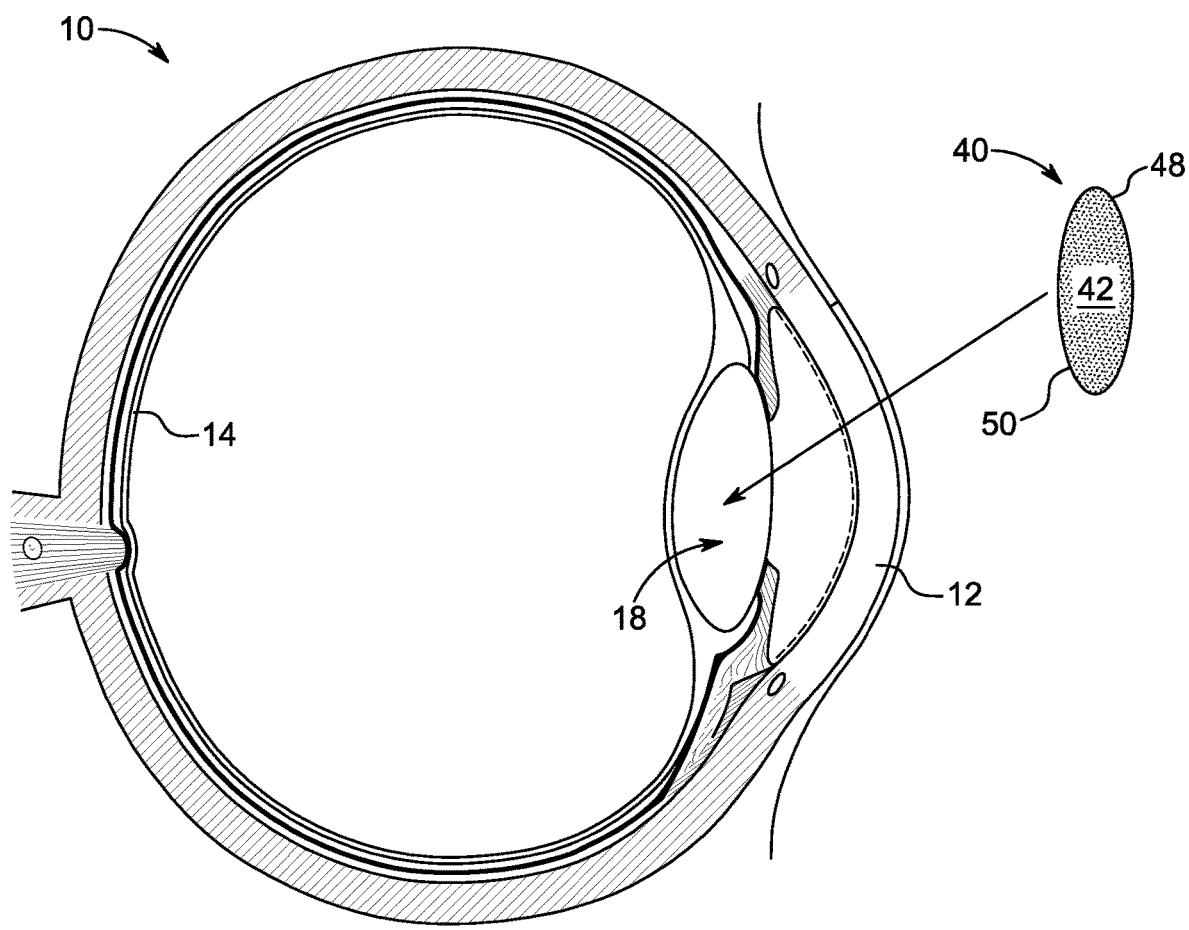
FIG. 2 is a schematic view of an embodiment of an eye with an intraocular implant device in accordance with the present disclosure positioned for installation into the open lens chamber of the eye.

The present disclosure provides a new type of implant device for installation into an empty lens chamber 18, as shown in FIG. 1. For example, as seen in FIG. 2, an intraocular implant device 40 is shown outside of the eye 10 for implantation into empty lens chamber 18 of eye 10. Intraocular implant device 40 includes an anterior side 48 positioned to face cornea 12 after implantation, and a posterior side 50 positioned to face retina 14 after implantation. Intraocular implant device 40 includes numerous technological innovations, and is operable to provide artificial sight improvement or sight restoration.

Intraocular Photoelectric Power Supply (IO-PEPS)

One aspect of intraocular implant device 40 provides an electrical power supply configured to generate electrical power for use by on-board electronics on the intraocular implant device 40 or alternatively housed within the eye. As such, the intraocular implant device 40 includes an intraocular photoelectric power supply (IO-PEPS) device.

Figure 3:
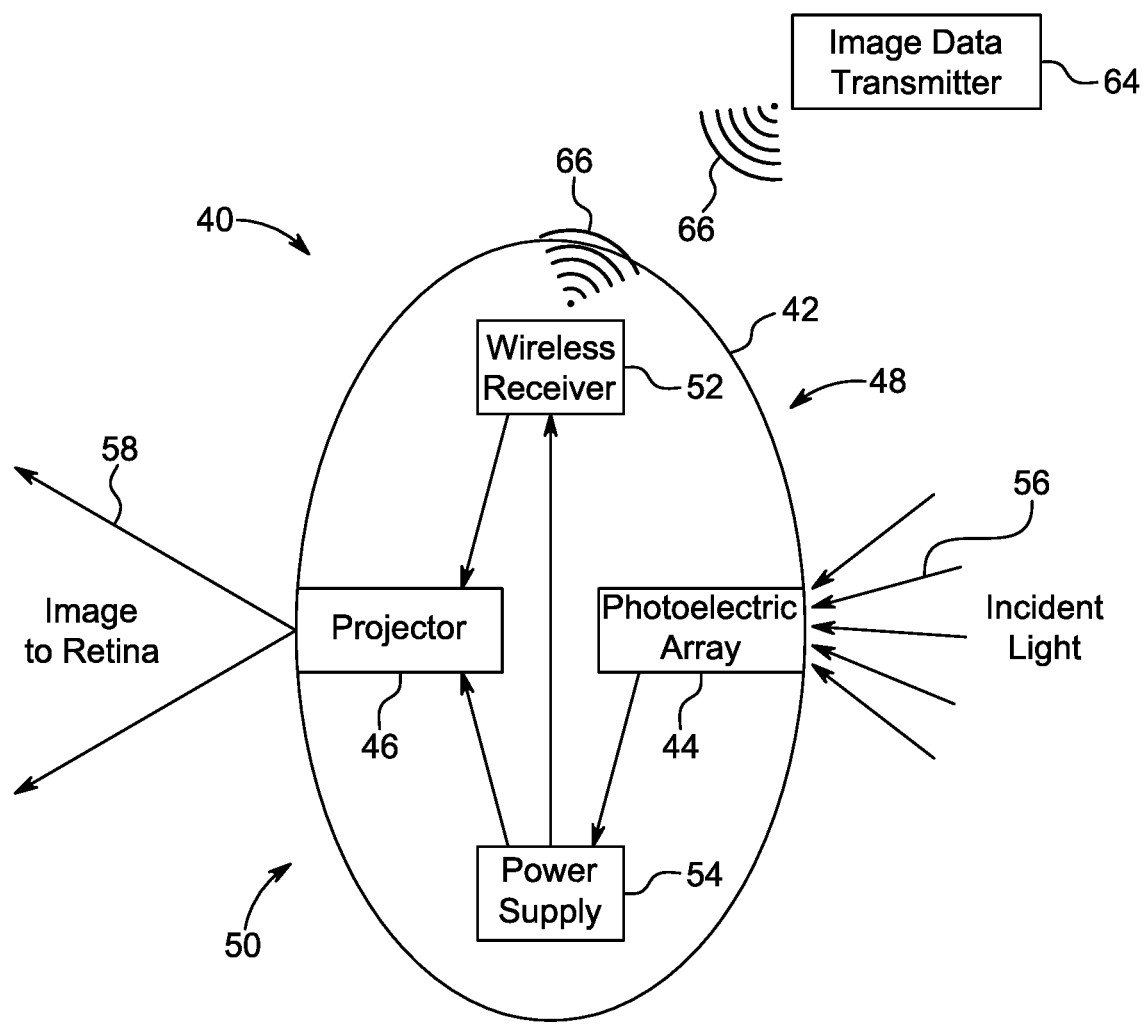
FIG. 3 is a schematic view of an intraocular implant device in accordance with the present disclosure.

As seen in FIG. 3, in some embodiments, intraocular implant device 40 includes a body 42 having an anterior side 48. A photoelectric array 44 including one or more photoelectric sensors is positioned on anterior side 48. Such sensors include any suitable photovoltaic or photoelectric sensors known in the art capable of converting incident light 56 received upon photoelectric array 44 into electricity. Photoelectric array 44 covers a portion of the surface of the anterior side 48 of implant device 40. Photoelectric array 44 includes at least one electrical output operable to transmit electric power to a circuit component. In some embodiments, photoelectric array 44 is coupled to a power supply 54, as shown in FIG. 3. Power supply 54 includes any suitable power converter or power storage device on intraocular implant device 40. Power supply 54 in some embodiments includes a battery configured for storing electrical power generated by photoelectric array 44 for later use by one or more other circuit components. Power supply 54 may be continuously recharging as additional incoming light is incident on photoelectric array 44 and also simultaneously distributing electrical power to other circuit components.

Intraocular implant device 40 is generally opaque when housed within the lens chamber 18 such that incident light 56 entering the eye does not pass optically through the lens body 42. Thus, all incident light entering the eye may be utilized by photoelectric array 44 for energy conversion. As such, the incident light 56 entering the eye may be manipulated to various characteristics for optimization of photoelectric conversion by photoelectric array 44. For example, in some embodiments, various photoelectric cells used in photoelectric array 44 provide improved energy conversion efficiencies when the incident light 56 has a chrominance in a spectral bandwidth tuned specifically to the properties of the photoelectric junctions.

Additionally, because the intraocular implant device 40 is generally opaque, and because the cornea may generally withstand greater luminance than the retina can, the incident light 56 may be further tuned to have increased luminance over natural light to further optimize energy conversion in photoelectric array 44. Thus, the incident light 56 may be generated using an external light source with modulated chrominance and luminance characteristics as compared to natural light to further improve power generation from the intraocular photoelectric power supply.

Your Eye as the Screen (YEATS)

One application of the IO-PEPS feature on an intraocular implant device 40 is to power a projector device 46, shown for example in FIG. 3, housed on the same implant device 40 or otherwise disposed within the eye 10. For example, projector 46 may include any suitable light emitter positioned within the eye in an orientation to project a generated image 58 onto the retina. The emitted light from the projector 46 is incident on the retina much in the way natural light may be incident on the retina after passing through the cornea and the lens. However, in patients with damaged cornea tissue or damaged lens tissue, by the time the light entering the eye makes it to the retina the light pattern is greatly distorted or blocked entirely, causing vision to be distorted or blurred, or causing blindness. By placing a rearward-facing projector 46 on an intraocular implant device 40, an artificial image may be projected onto the retina to simulate natural light, thereby allowing a user to see the artificial image generated by the projector much like the patient would see normally using natural light. A significant difference is that, when using projector 46, the generated image 58 may be controlled to include image data from any source, so the patient's vision may be enhanced or replaced entirely over the field of view available from natural light.

During use, projector 46 is powered by electric power generated on-board the intraocular implant device 40 using photoelectric array 44. Photoelectric array 44 generates enough electric power to operate projector 46 either directly, or through a power supply 54. In some applications, projector 46 may be turned off remotely while allowing photoelectric array 44 to charge power supply 54. Once a sufficient amount of energy is stored in power supply 54, projector 46 may be turned on wirelessly, and photons may be emitted by projector 46 using one or more light emitters. The generated image 58 is then illuminated onto retina 14 through the eye. The retina 14 processes the incident light much like it would natural light, forming an image in the brain and allowing a user to perceive the image.

Figure 4:
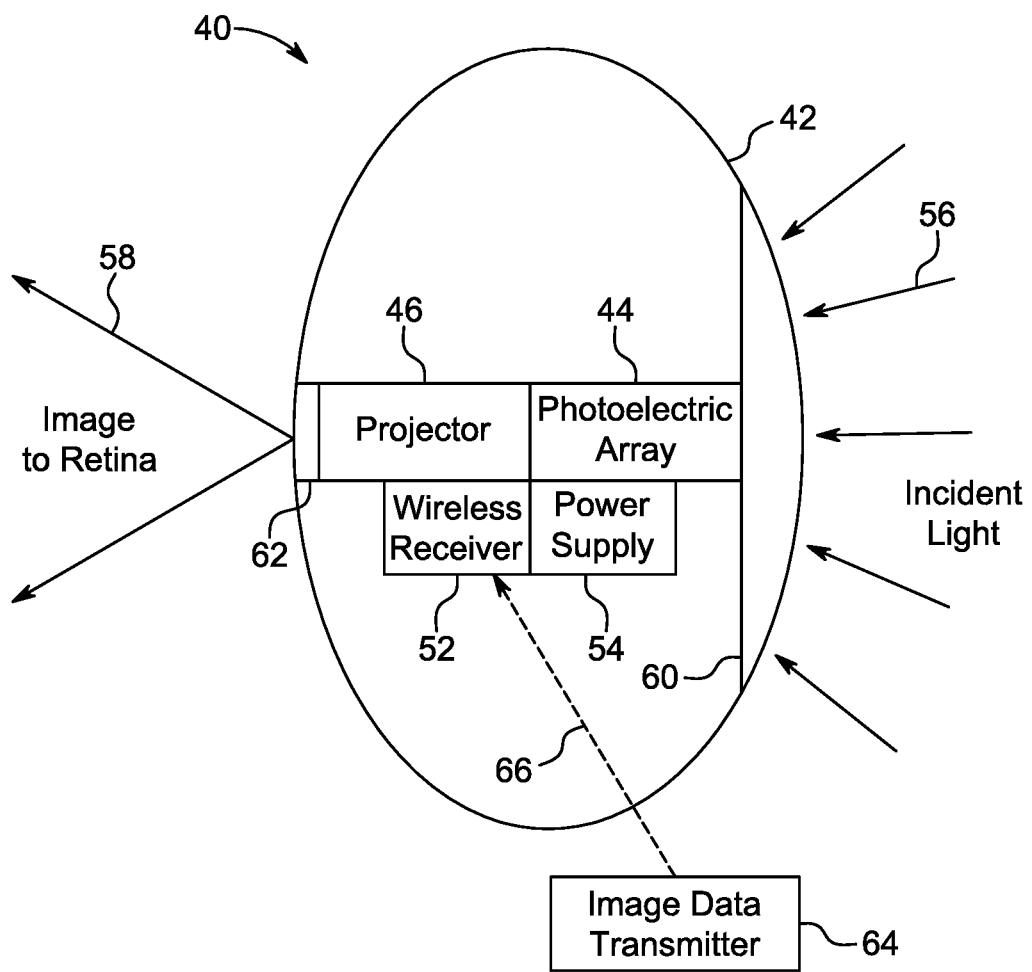
FIG. 4 is a schematic view of an intraocular implant device in accordance with the present disclosure.

The generated pattern of photons or a generated image 58 projected onto the retina 14 is generated by projector 46 using an input signal 66 received by a wireless receiver 52 in some embodiments, as seen in FIG. 3 and in an alternative embodiment in FIG. 4. Input signal 66 includes information associated with the photon pattern to be generated by one or more light emitters within projector 46. Thus, the projector 46 is configured to receive a digital input signal including the image data, and to emit photons from the light projector onto the retina in a pattern representative of the image data. The input signal 66 is passed to intraocular implant device 40 wirelessly from a remote transmitter 64. The input signal 66 is passed to a wireless receiver 52 housed on-board the implant device 40 or alternatively housed at another location within the eye. In some embodiments, wireless receiver 52 is integrated onto projector 46 such that the two are combined as a single unit with wireless data receiver or transmission capabilities. Image data transmitter 64 includes any suitable external device for communicating an input signal 66 to intraocular implant device 40, and specifically to wireless receiver 52 on intraocular implant device 40. Any suitable wireless signal transmission protocol for transmitting data or analog signals associated with imagery may be used for input signal 66.

Once the input signal 66 is received by intraocular implant device 40, the signal is passed to the projector 46, and the projector executes instructions associated with the signal to generate photons representative of an image to be displayed on the retina. In some embodiments, the input signal 66 corresponds to photographs, text, illustrations, videos or any other image data.

As shown in FIG. 3 and FIG. 4, in various embodiments, power supply 54 is also connected to wireless receiver 52 in some embodiments. Thus, power supply 54 may simultaneously supply power to projector 46 and to wireless receiver 52, if necessary. Alternatively, in some embodiments, photoelectric array 44 provides generated electricity directly to wireless receiver and projector.

Wireless receiver 52 may be positioned at any suitable location on intraocular implant device 40, including on a common circuit board structure with one or more other circuit components, such as but not limited to power supply 54, projector 46, photoelectric array 44 or other components. In some embodiments, one or more antennae are connected to wireless receiver 66 to enhance reception of input signal 66 from image data transmitter 64. In some embodiments, the device may be configured to provide enhanced low-light vision or night vision by using an external image data source that acquires an image using a material that responds more quickly than the retina, or by using a material that selectively processes incoming light with higher sensitivity.

One aspect of the present disclosure provides a system that may improve vision over natural analog vision. For example, when natural light enters the eye, the light incident on the retina is limited by the amount of light entering through the cornea and lens. However, using projector 46, additional, higher resolution light patterns may be projected onto the retina to improve or enhance vision over natural analog vision.

Artificial Vision System

Figure 5:
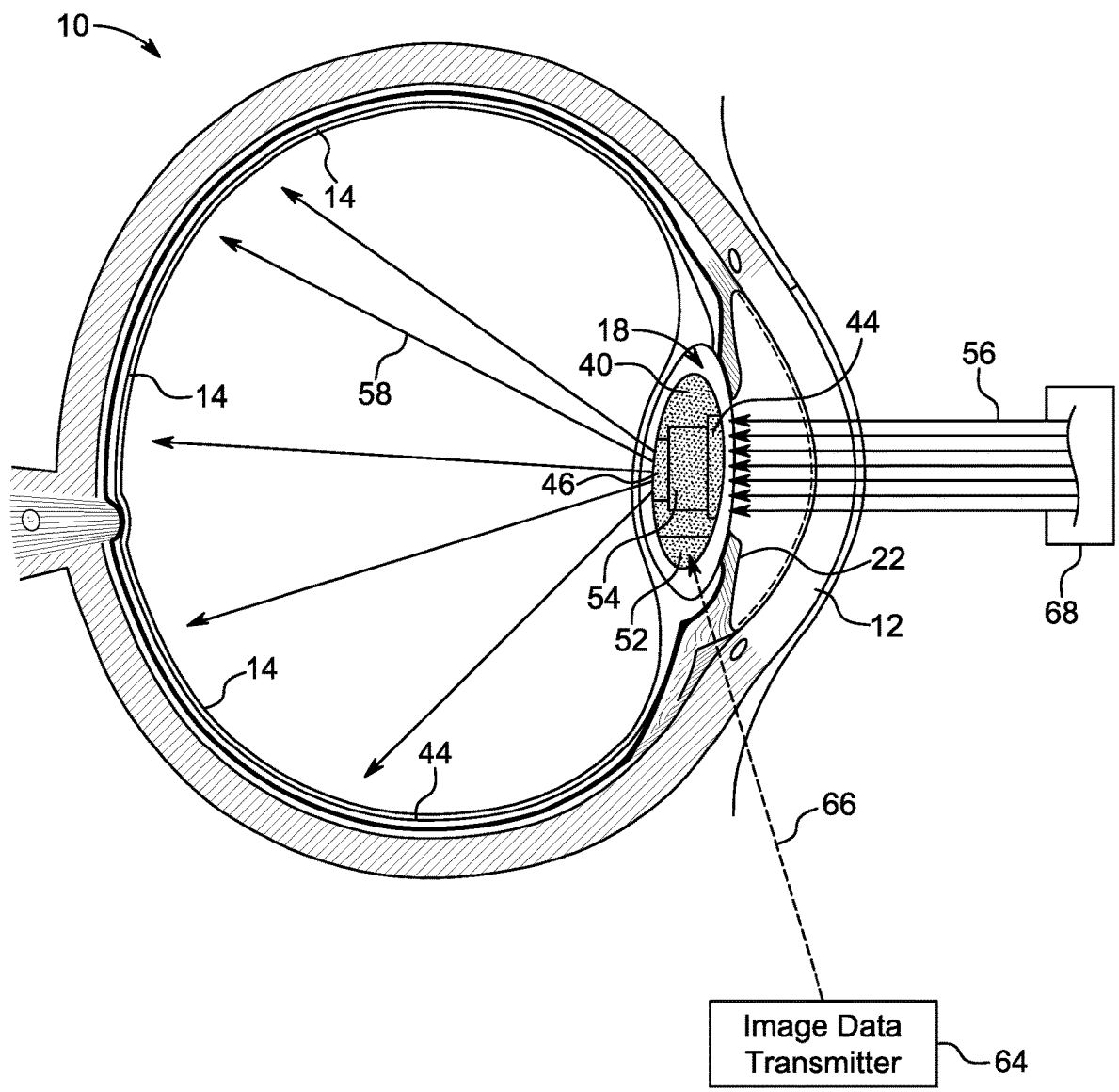
FIG. 5 is a schematic view of an embodiment of an eye with an intraocular implant device in accordance with the present disclosure installed in the lens chamber, and an external light source irradiating the anterior side of the intraocular implant device through the cornea.

Referring now to FIG. 5, an artificial vision system includes an intraocular implant device 40 including an intraocular photoelectric power supply, including a photoelectric array 44 disposed on the anterior side of implant device 40 facing toward the cornea 12. Additionally, a projector 46 is disposed on the posterior side of implant device 40 facing the retina 14. An external light source 68 generates a beam of artificial incident light 56 directed toward the cornea. The generated artificial light 56 is produced solely for the purpose of powering the intraocular photoelectric power supply housed on intraocular implant device 40 installed in the lens chamber 18 within the eye 10. The generated artificial light 56 is tuned in both chrominance (wavelength and frequency) and luminance (brightness) to provide optimized energy conversion and electric power generation inside the photoelectric array 44. The power generated by photoelectric array 44 is used to charge power supply 54, and is subsequently used to power projector 46 to generate a pattern of photos or a generated image 58 for irradiation of the retina 14. Thus, the only light incident on the retina 14 is the light generated by the projector 46.

An external transmitter 64 sends a wireless input signal 66 to intraocular implant device 40. Input signal 66 is received by a wireless receiver 52 on the implant device 40, and the input signal 66 is passed to projector 46 to determine the pattern of generated photons or a generated image 58 projected onto retina 14 by projector 46. Input signal 66 can include data packets corresponding to image data from any source, such as an external camera.

As seen in FIG. 5, the incident light beam 56 generated by external light source 68 is collimated in some embodiments to align with the opening of the iris 22 such that the light will be incident on the photoelectric array 44. In some embodiments, photoelectric array 44 is dimensioned to correspond to the surface region on the body 42 of intraocular implant device 40 aligned with the circular opening defined by the iris 22.

Figure 6:
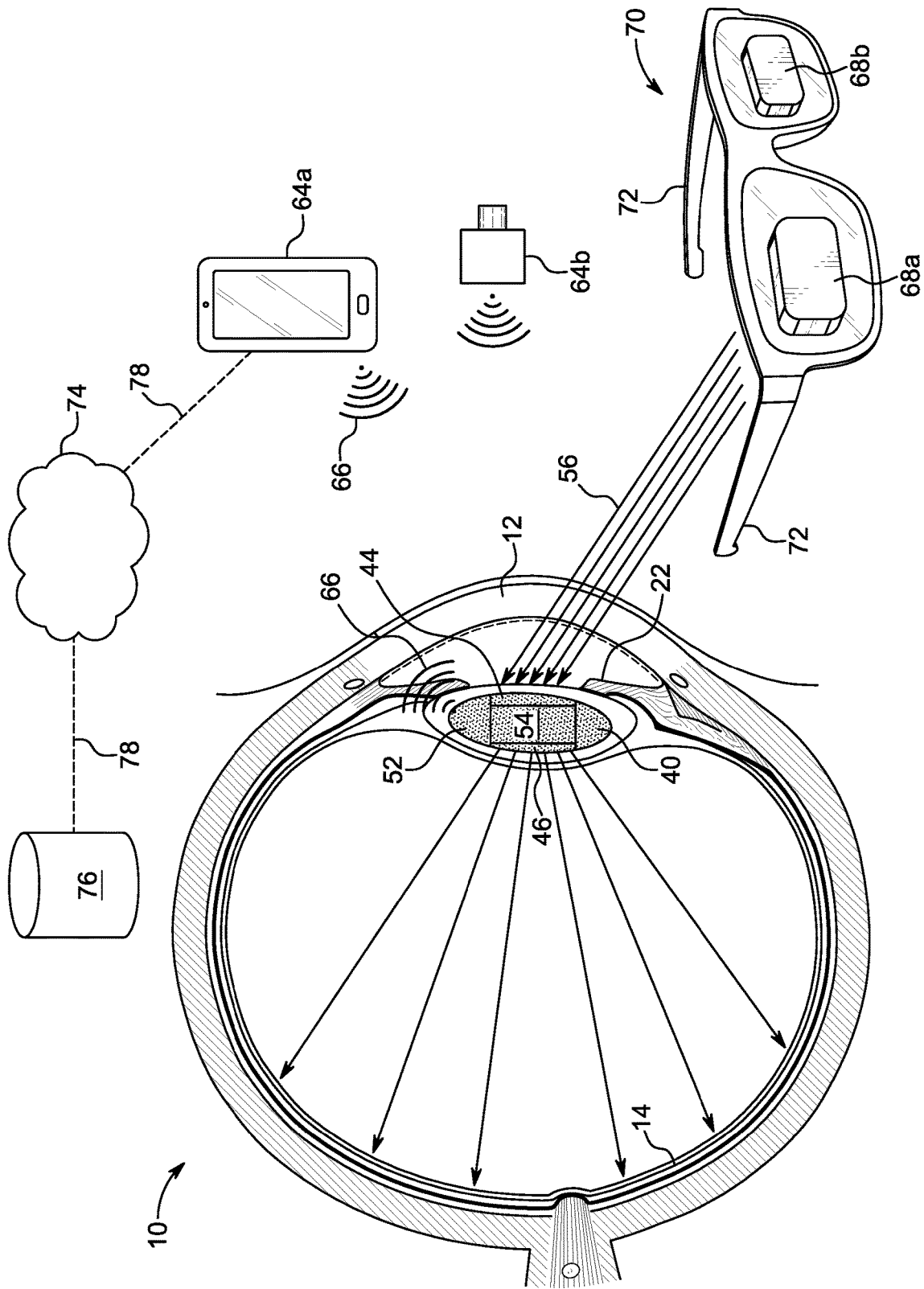
FIG. 6 is a schematic view of an embodiment of an eye with an intraocular implant device in accordance with the present disclosure installed in the lens chamber, and an external light source irradiating the anterior side of the intraocular implant device through the cornea while the intraocular implant device receives a wireless image data signal from a remote transmitter.
Figure 7:
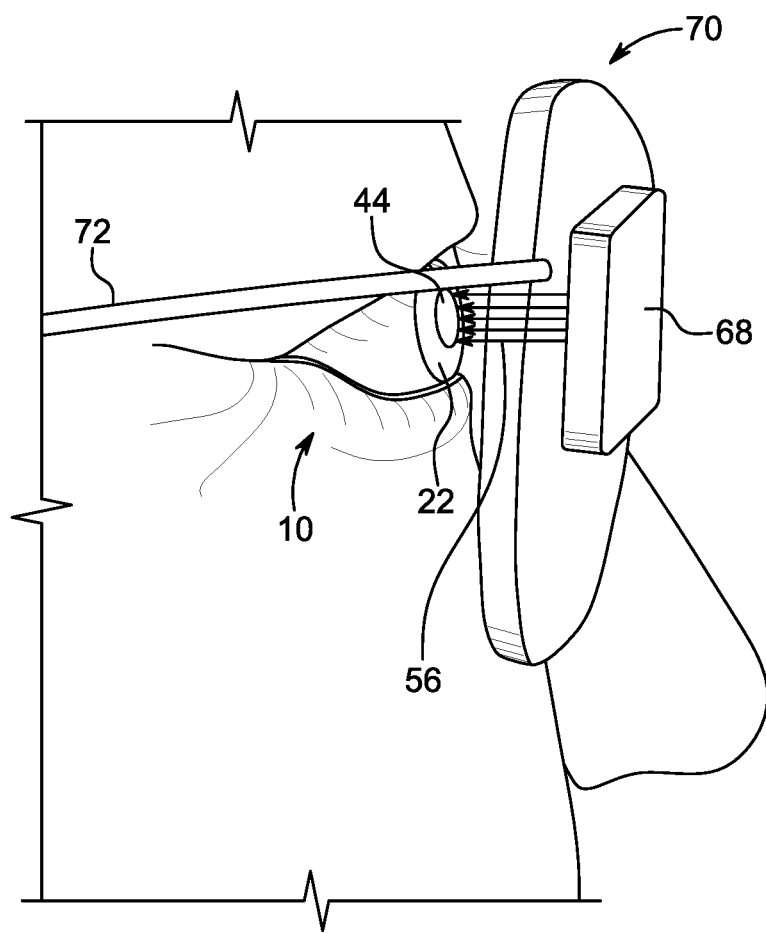
FIG. 7 is a schematic view of an embodiment of an intraocular implant device including an intraocular photoelectric power supply and an external light source irradiating light through the cornea onto the photoelectric array included on the implant installed in the lens chamber in the eye.

Referring to FIG. 6 and FIG. 7, in additional embodiments, external light source 68 may include a wearable technology including one or more light emitters spaced from the eye 10 and configured to emit light back toward the eye 10 for the specific purpose of powering one or more intraocular photoelectric power supply (IO-PEPS) devices housed in the lens chamber 18 in one or both eyes. For example, in some embodiments, a wearable eyeglass frame 70 includes a first external light source 68a and a second external light source 68b. Frame 70 includes first and second temples 72 positioned to engage a user's head, as shown in FIG. 7. Each external light source 68 emits a beam of artificial light back toward the user's eye 10. The beam of generated external light 56 passes into the eye through the cornea 12, and is incident on the photoelectric array 44 on intraocular implant device 40 housed in lens chamber 18. The external light source 68 includes any suitable source of light for powering photoelectric array 44. The light emitted by external light source 68 does not pass directly through the eye to the retina. Instead, the light is converted into electrical energy via the photoelectric array 44, and is then subsequently converted back into photons using projector 46 to project a desired pattern corresponding to an image onto the retina 14.

As shown in FIG. 6, the image generated by projector 46 may come from many different sources. In some embodiments, transmitter 64a includes a mobile device such as a cell phone, laptop, tablet computer, television, or other external electronic device. In some embodiments the transmitter 64a is a video camera which transmits a video feed. Transmitter 64a may include locally stored image data to be used for input signal 66. Alternatively, transmitter 64a may connect dynamically to a remote image storage database 76 via a network, or cloud 74 to access content for input signal 66. In some embodiments, digital image content, such as movies, images, etc. are streamed from a remote database 76 via a network 74 using network signals 78 to provide access to image data for input signal 66.

Referring further to FIG. 6, in some embodiments, an external camera 64b is also configured to produce an input signal 66. The camera 64b is positioned to acquire image data associated with the camera's field of view. The camera 64b may be local to a user, for example may be installed on eyeglass frame 70, or the camera 64b may be remote such that the field of view of the camera is not in the vicinity of the user. The artificial vision system allows a user to dynamically change the input on projector 46 such that the projector 46 may select to display an image pattern associated with input signal 66 from first transmitter 64a or alternatively from camera 64b. In additional embodiments, camera 64b may instead include a second transmitter such as a cell phone, smart phone, laptop, tablet computer, television, or other external electronic device. In some embodiments, projector 46 includes multiple input channels, and is selectively operable to display image data associated with each separate channel, thereby allowing a user to switch between input signals from different external image data sources.

Non-Medical Uses

The above referenced devices may also be utilized for non-medical applications such as consumer entertainment, professional vision augmentation, virtual reality content generation and display, military applications, or other nonmedical applications. For example, in some embodiments, a user with an intraocular implant device 40 installed in one eye is able to selectively turn on the device to receive image data from any external source via input signal 66. The user may be able to maintain a natural lens in the second eye to continue to rely on natural analog vision when not using device 40. As such, the intraocular implant device 40 provides an implantable brain-machine interface capable of delivering digital image content to the user through an image projected directly onto the retina 14. The image may be manipulated in many ways prior to projection by projector 46 that are not possible via standard analog light transmission through the cornea and lens. This makes enhanced, augmented and artificial vision possible.

Medical Uses

The above-referenced devices may also be used in medical applications for sight restoration or sight improvement. In such medical applications a patient may receive an intraocular implant device 40 in the lens chamber of each eye. The patient may then utilize a wireless transmitter 64 to transmit image data from an external source to each intraocular implant device 40. The transmitter 64 includes a camera oriented toward the user's local environment in some applications simulating natural vision. Alternatively, transmitter 64 includes an auxiliary input from some other source of digital image content, such as computer, mobile phone, tablet or other source. Medical patients with conditions such as cornea damage may primarily rely on the intraocular implant devices 40 to provide artificial vision where natural analog vision simply is no longer possible due to the inability of light to properly enter and pass through the eye to the retina.

The present disclosure further provides associated methods of modifying, improving, restoring, augmenting or restoring vision in humans and animals using the previously-described devices and techniques. For example, a method of restoring vision in an eye comprises the steps of: (1) providing an intraocular implant device including an anterior side and a posterior side, a photoelectric array on the anterior side, and a projector on the posterior side; (2) positioning the intraocular implant device in the lens chamber of the eye such that the photoelectric array faces the cornea and the projector faces the retina; (3) illuminating the photoelectric array with input light from an external light source; (4) converting the input light into electrical energy via the photoelectric array; (5) powering the projector using the electrical energy converted by the photoelectric array; and (6) projecting photons generated by the projector onto the retina, wherein the projected photons correspond to digital image data received wirelessly by the intraocular implant device from a remote transmitter. The method may further comprise sending a wireless input signal to the projector from an external transmitter, wherein the wireless input signal contains image data; emitting photons from the projector in a pattern representative of the image data; providing an external light source positioned to emit light towards the photoelectric sensor; receiving the light in the photoelectric sensor; converting the light into electrical energy; and powering the intraocular implant device with the electrical energy.

Photoelectric Power Harnessing Camera (PEP-Cam)

Now referring to FIGS. 8-21, other embodiments may include a combination of an intraocular projector 46 powered by an intraocular photoelectric power supply (IO-PEPS) 54 where the image collector 64 or camera is integrated with the photoelectric power supply 54 (a power harnessing digital camera 80). In alternative embodiments, the power harnessing digital camera may provide either color or grayscale images. Thus, the photoelectric array 44 is both collecting the light 56 to power the intraocular device 40 as well as collecting the image data for the images 66 that will be projected onto the retina 14. Both the photoelectric array 44 and the camera 64b perform a photoelectric conversion of light energy incident on the elements of the array 44 into electrical energy for use with one or more circuit components disposed on the intraocular implant body. Generally, a digital camera 64b detects the luminance and chrominance at each picture element (or pixel) and disregards the photoelectric power content of the light, whereas a photoelectric array 44 aggregates the photoelectric energy generated across the element array and disregards the luminance and chrominance of the incident light at individual points or picture elements of the array.

In one embodiment, the photoelectric array 44 and the digital camera 64b are functionally combined into the same device with a shared array, sharing a common light stream 56. Several methods may be employed to achieve the capturing of both the image, which can then be transmitted, and the energy to power the intraocular device 40. In some embodiments, the device is configured to generate color images.

Figure 8A:
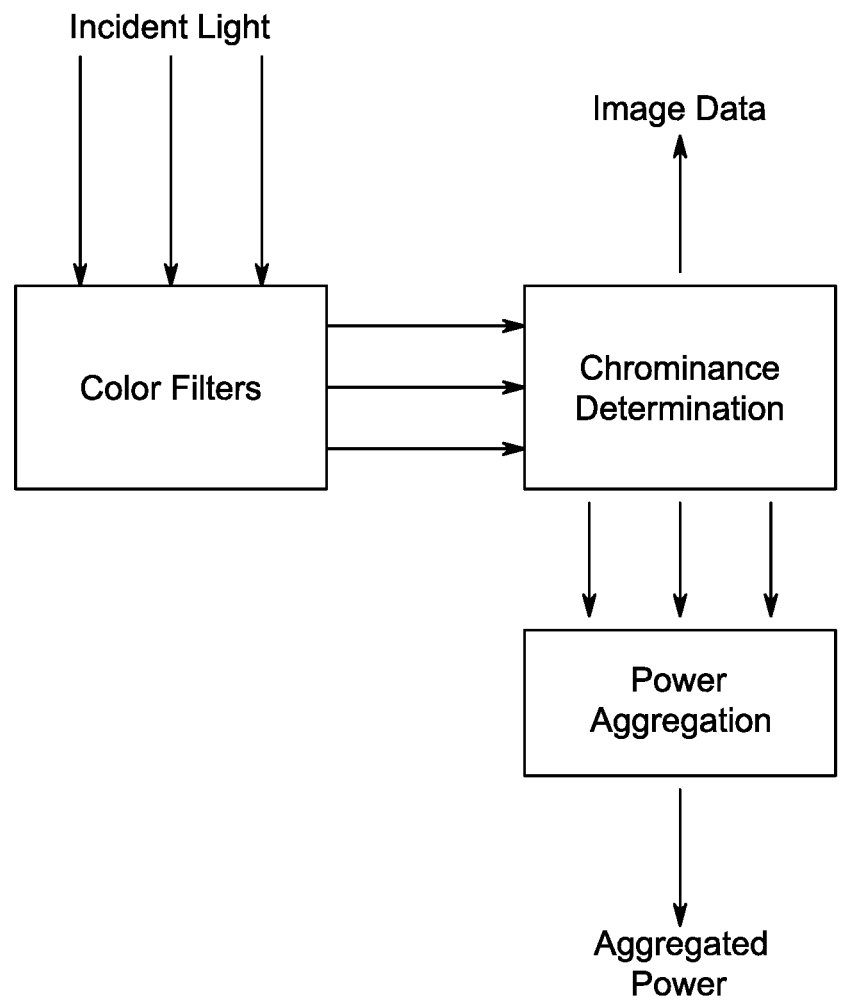
FIG. 8a is a schematic view of a power harnessing digital camera using color filters for light color division.

Referring to FIG. 8a, a first embodiment divides the photoelectric collector array 44 into individual picture elements (pixels). Many digital cameras 64b use color filters in conjunction with each picture element to filter certain wavelengths of light out. Each picture element has an overlay of color filters, typically red, green, and blue, thus, when incident light 56 enters the apparatus, each picture element is able to measure the amount of light 56 entering in the red spectrum, the green spectrum, and the blue spectrum. In the power harnessing camera, a power aggregation layer may be positioned posterior each picture element or color energy measurement layer. The photoelectric element under each color filter may be optimized for the color or frequency of light for which the corresponding color filter is configured to measure, thus capturing the light energy that is activating the picture elements.

Figure 8B:
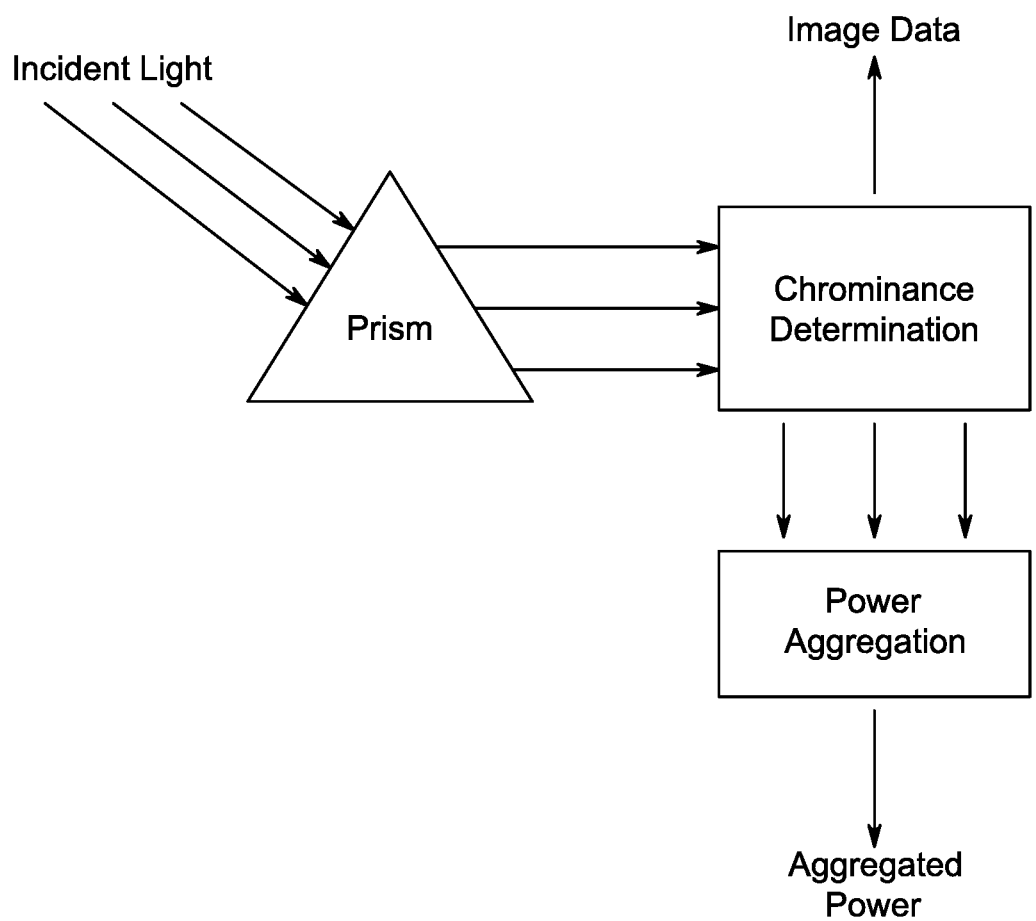
FIG. 8b is a schematic view of a power harnessing digital camera using prisms for light color division.

Referring to FIG. 8b, a second embodiment uses a similar system of capturing the chrominance by utilizing individual picture elements, however, color filters are substituted by prism 110 which separates the light into a spectrum. The subdivided light energy components (red, green, and blue) can be measured to determine the picture elements chrominance for each image cycle while all of the light energy can be harnessed by the photoelectric array positioned behind the prism. Thus, instead of filtering which reduces the total light and frequencies being received by each element of the photoelectric array, the full spectrum of incident light 56 may be collected.

Figure 9:
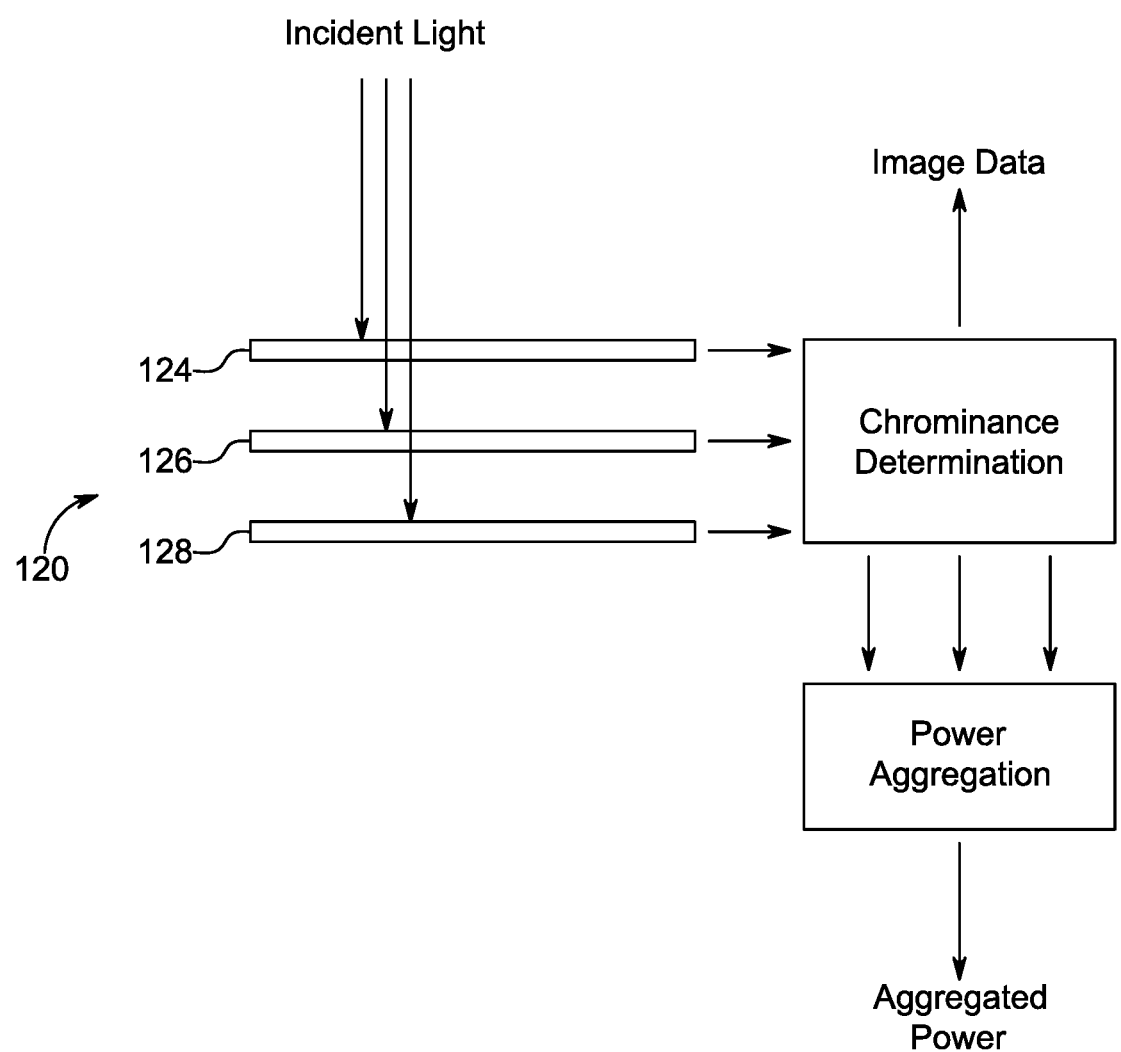
FIG. 9 is a schematic view of power harnessing digital camera using a stacked multi-junction array for chrominance determination.

Referring to FIG. 9, a third embodiment may utilize multilayer (multi-junction) photoelectric cells 120. The multi-junction photoelectric device may comprise layers of stacked photoelectric p-n junctions wherein each junction is receptive to a specific bandwidth of light frequencies and permits other bandwidths of light to pass through. A first layer comprises an incident light surface 124. An incident light surface 124 is selected to allow photons which have an energy level below a first specified frequency to pass through the incident light surface but captures photons having an energy level above the first specified frequency. A second layer 126, positioned below the incident light surface is selected to allow photons which have a second energy level below a second specified frequency to pass through the second layer, wherein the layer captures photons at a frequency between the first specified frequency and the second specified frequency. In this manner, a plurality of layers 124, 126 may be stacked to capture light within a large spectrum. The layers 124, 126, 128 are stacked in descending magnitude of frequency, which allows light energy corresponding to a receptive frequency of each junction to be captured by each individual layer. Photoelectric layers 124, 126, 128 that are individually receptive to blue, green, and red may be used in a stack to form the basis of a picture element. This configuration provides for chrominance determination while permitting energy capture that is optimized in the frequency band of each individual layer, thus harvesting energy across a full spectrum of light waves. The multilayer or multi-junction photoelectric array may also provide higher pixel densities and image resolution.

Figure 23:
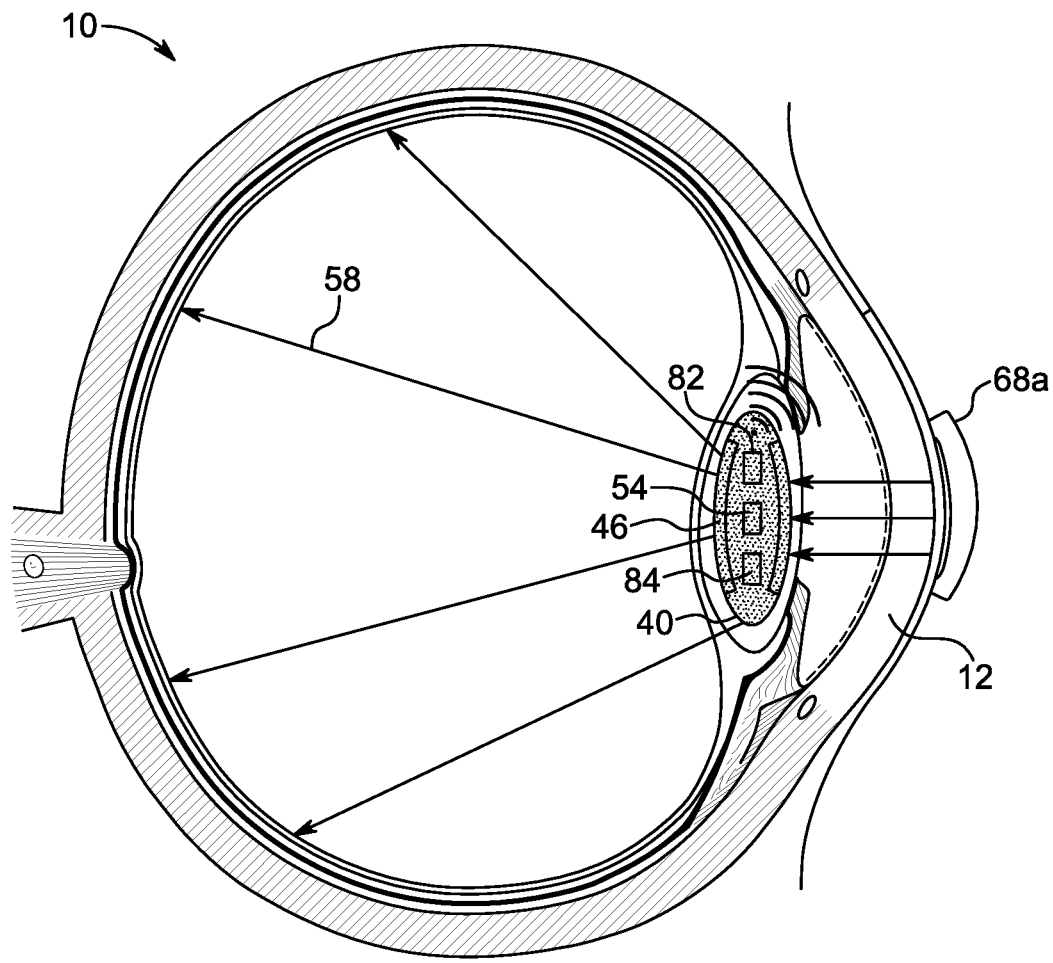
FIG. 23 is a view of an exemplary system having an intraocular implant device being recharged by an optimized light source on a contact lens.

Optimized light power may be supplied to the intraocular device 40 by placing a rechargeable, optimized light-power source 68 on the inside of a rechargeable epicorneal or extraocular device 90, such as but not limited to a scleral contact lens. This allows the device 40 to receive power even when the user's eye 10 is closed. Thus, a light emitting contact lens may be worn by a user to charge the intraocular device as in FIG. 23. A rechargeable, optimized light-power source 68 may also be placed on a spectacle-like device 70 with light aimed at the pupil of a user. These extraocular power sources may selectively comprise a camera 64b and transmitter on the front. These optimized light power sources may be necessary for situations in which the photoelectric array 44 is not capturing a sufficient amount of energy to power the intraocular device 40. Thus, these periods of intensified charging may allow the intraocular device 40 to receive sufficient energy to recharge the internal power supply 54 on the device 40. The extraocular power source may be removed and recharged.

Figure 10:
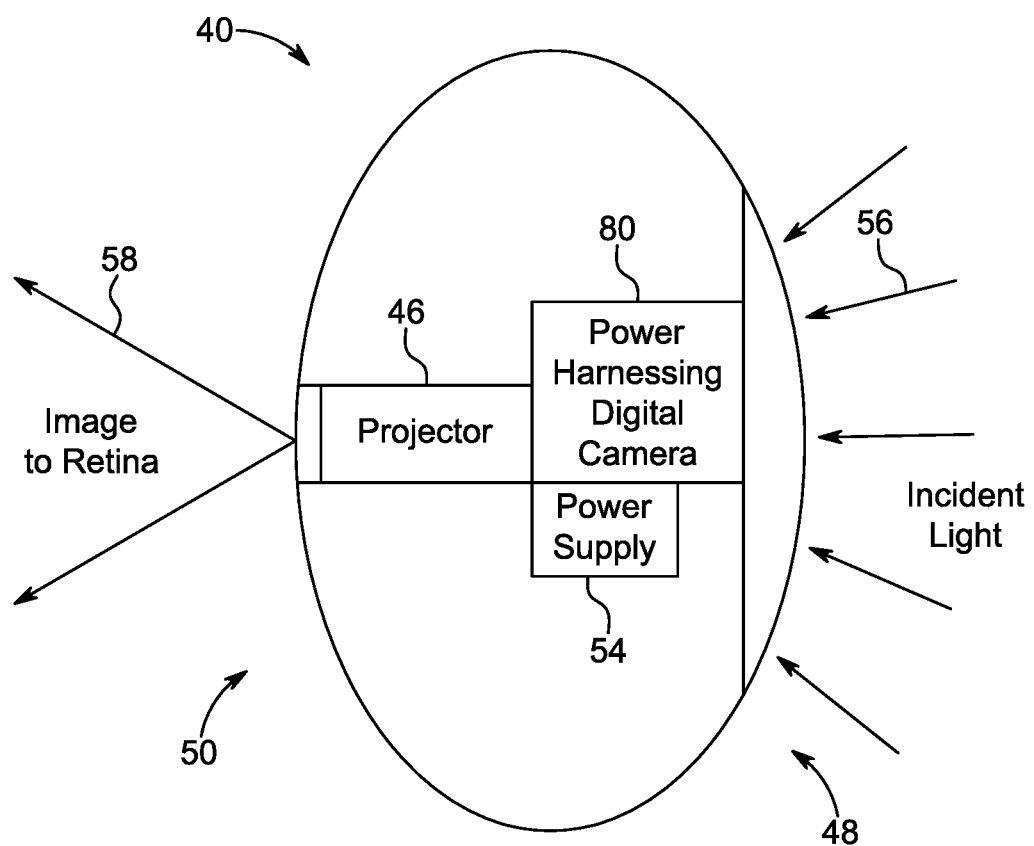
FIG. 10 is a schematic view of an intraocular implant device with an power harnessing digital camera, power supply, and a projector.
Figure 11:
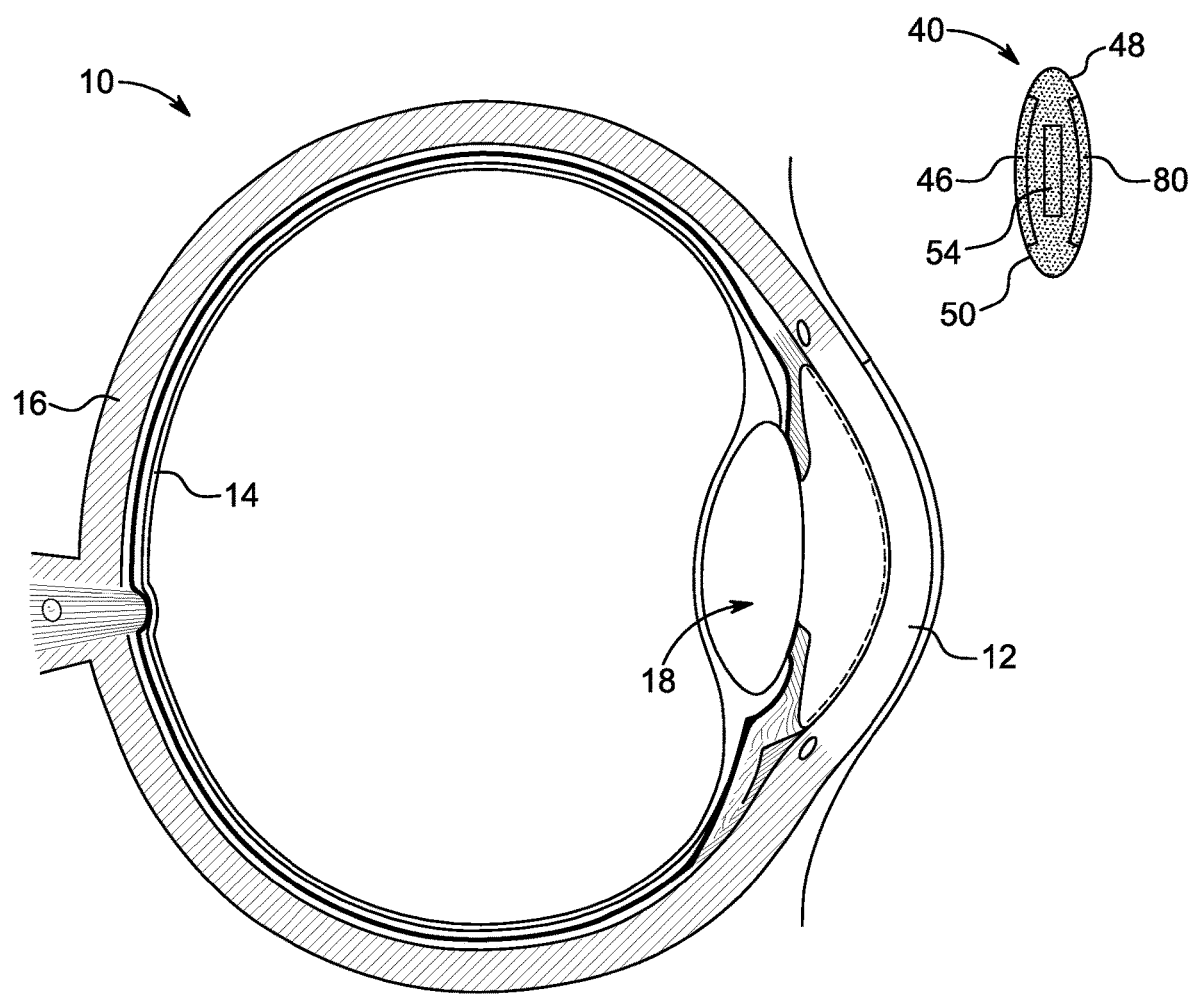
FIG. 11 is a schematic view of an intraocular implant device with an power harnessing digital camera, power supply, and projector before implantation into the lens cavity.
Figure 12:
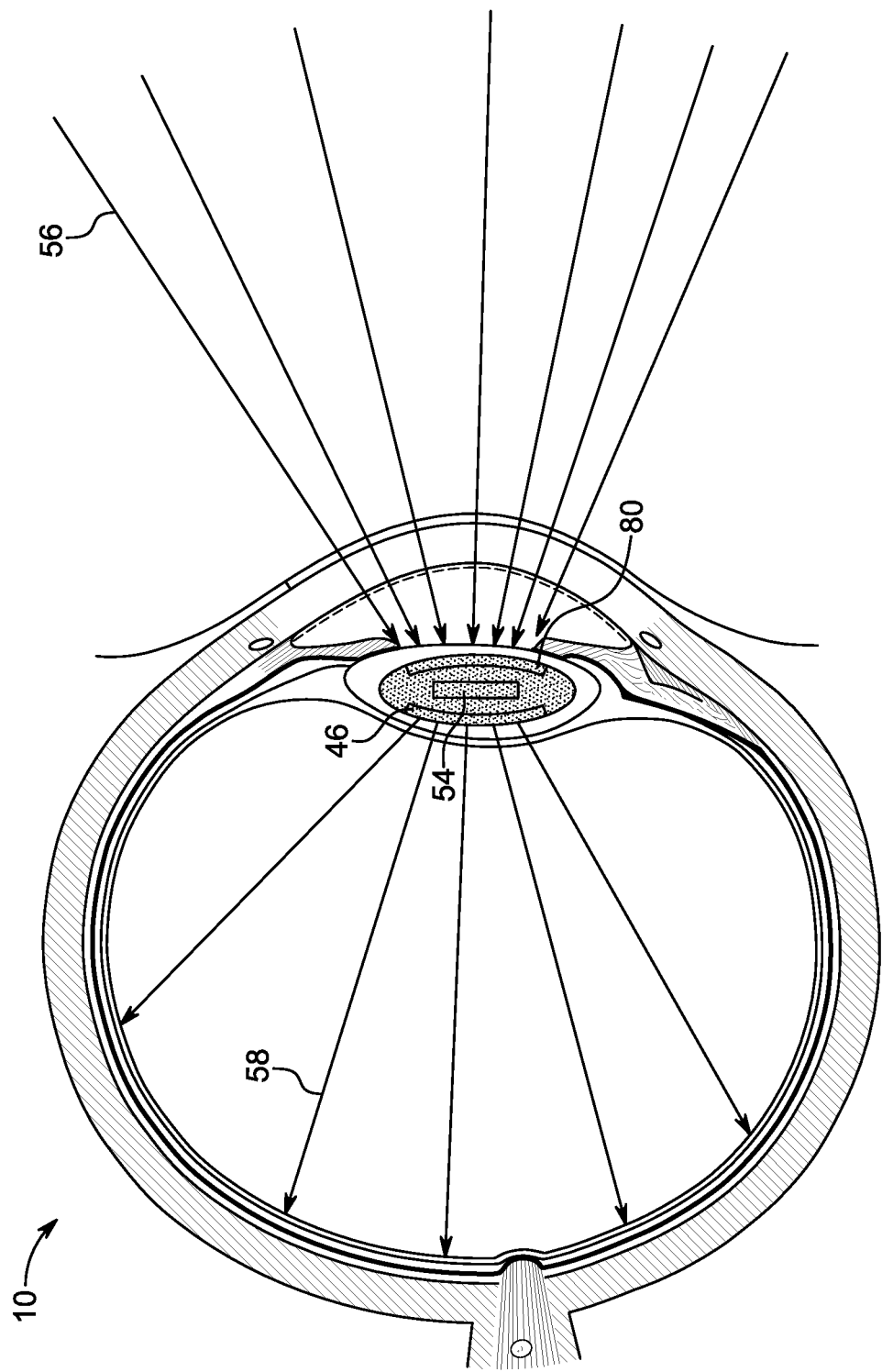
FIG. 12 is a schematic view of an intraocular implant device with an power harnessing digital camera, power supply, and projector after implantation into the lens cavity.

Referring to FIG. 10, in some embodiments, the intraocular device 40 comprises a power harnessing digital camera 80, a power supply 54, and a projector 46. The power harnessing digital camera 80 is positioned on the anterior side 48 of the intraocular device 40 proximate the cornea 12 and the projector 46 is positioned on the posterior side 50 of the intraocular device 40 facing the retina 14 of a user. Incident light 56 will travel through the cornea 12 of a user to the power harnessing digital camera 80 which will capture the luminance and chrominance of pixels, create a digital image, and capture photoelectric energy. The energy will be transferred from the power harnessing digital camera 80 to the power supply 54. The digital image will be transmitted to the projector 46. The projector 46 will receive power from the power supply 54 and then project the digital image received from the power harnessing digital camera 80 onto the retina 14 of a user. This integrated system allows a user to process images in a more natural manner. The eye itself will control the direction of the camera 46b for the frame of reception of images. The power harnessing digital camera 80, the power supply 54, and the projector 46 are all mounted on the intraocular device 40 which may be implanted into the lens chamber 18 of a user.

Figure 13:
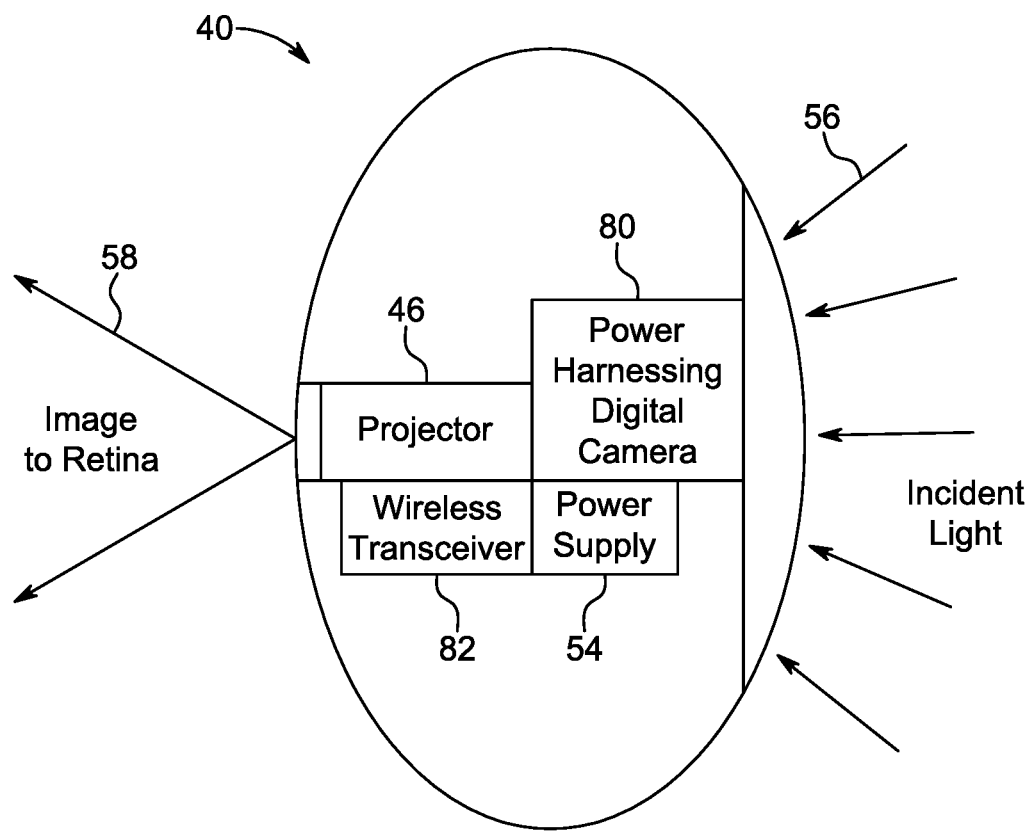
FIG. 13 is a schematic view of an intraocular implant device with a power harnessing digital camera, power supply, projector, and wireless transceiver.
Figure 14:
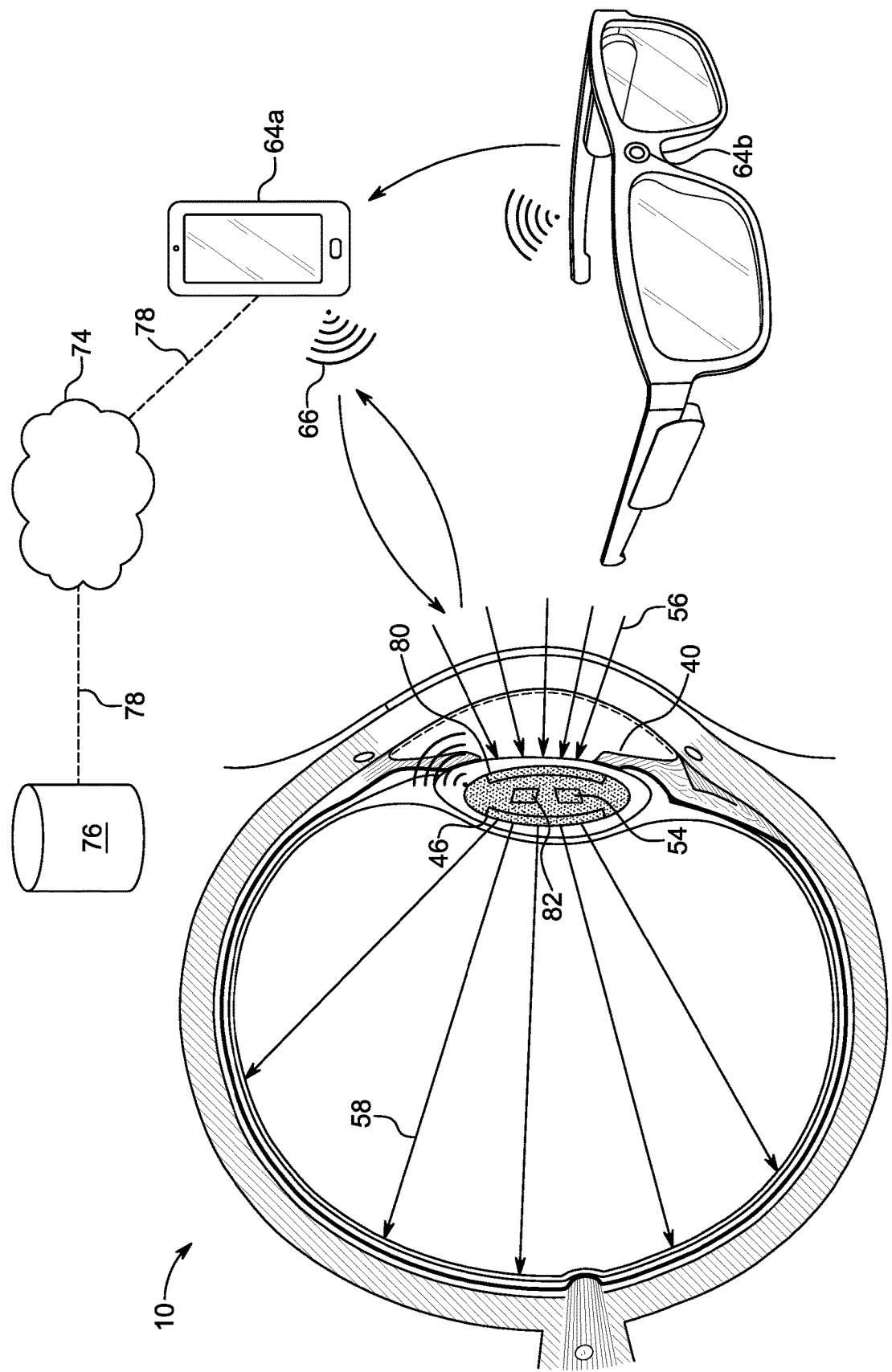
FIG. 14 is a view of an exemplary system having an intraocular implant device with a power harnessing digital camera, power supply, projector, and wireless transceiver receiving data from an external device.
Figure 15:
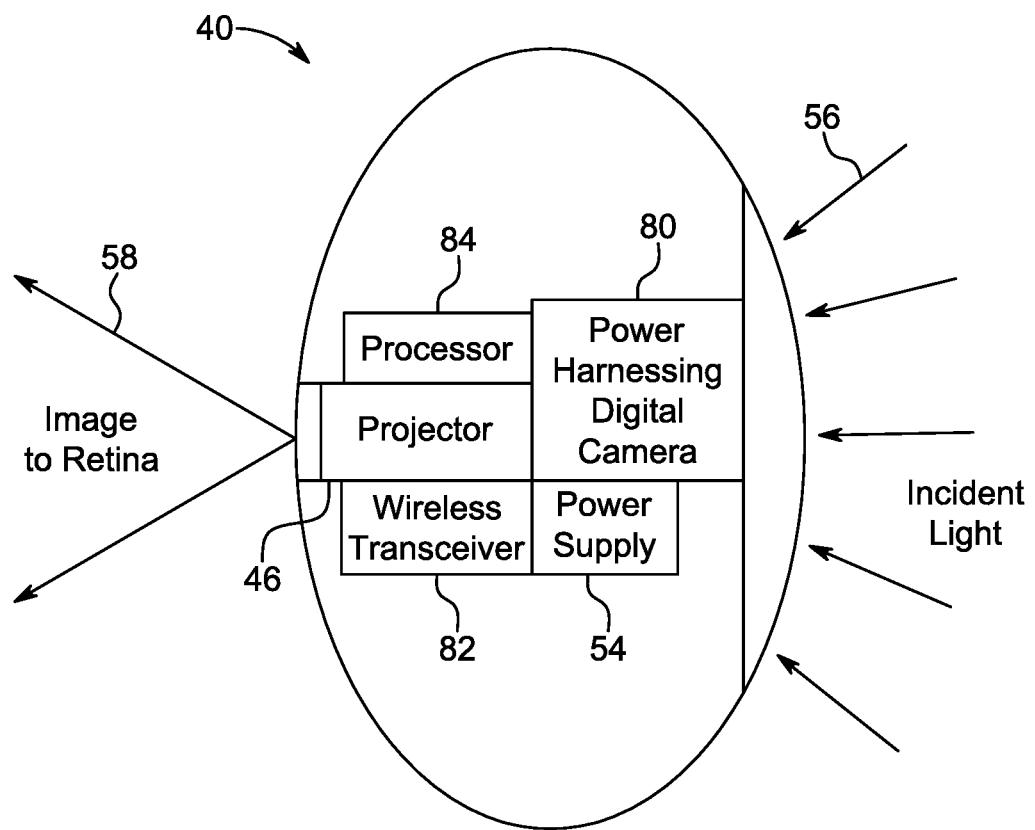
FIG. 15 is a schematic view of an intraocular implant device with a power harnessing digital camera, power supply, projector, wireless transceiver, and processor.
Figure 16:
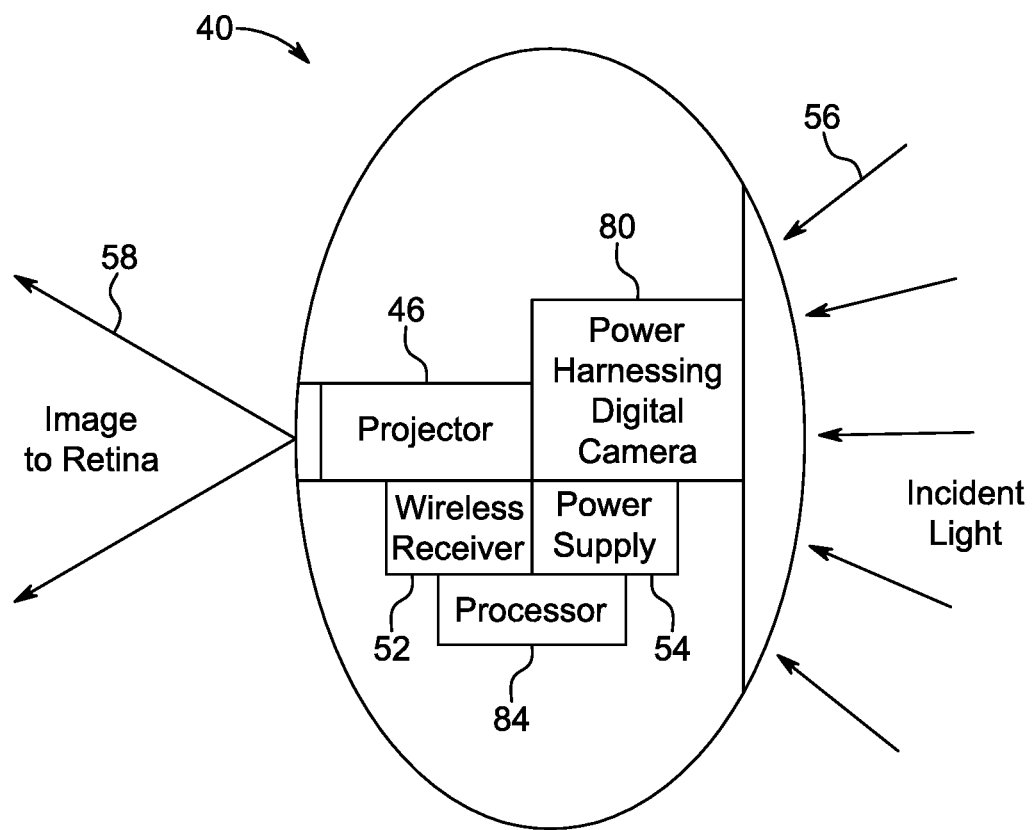
FIG. 16 is a schematic view of an intraocular implant device with a power harnessing digital camera, a power supply, projector, wireless receiver, and processor.
Figure 17:
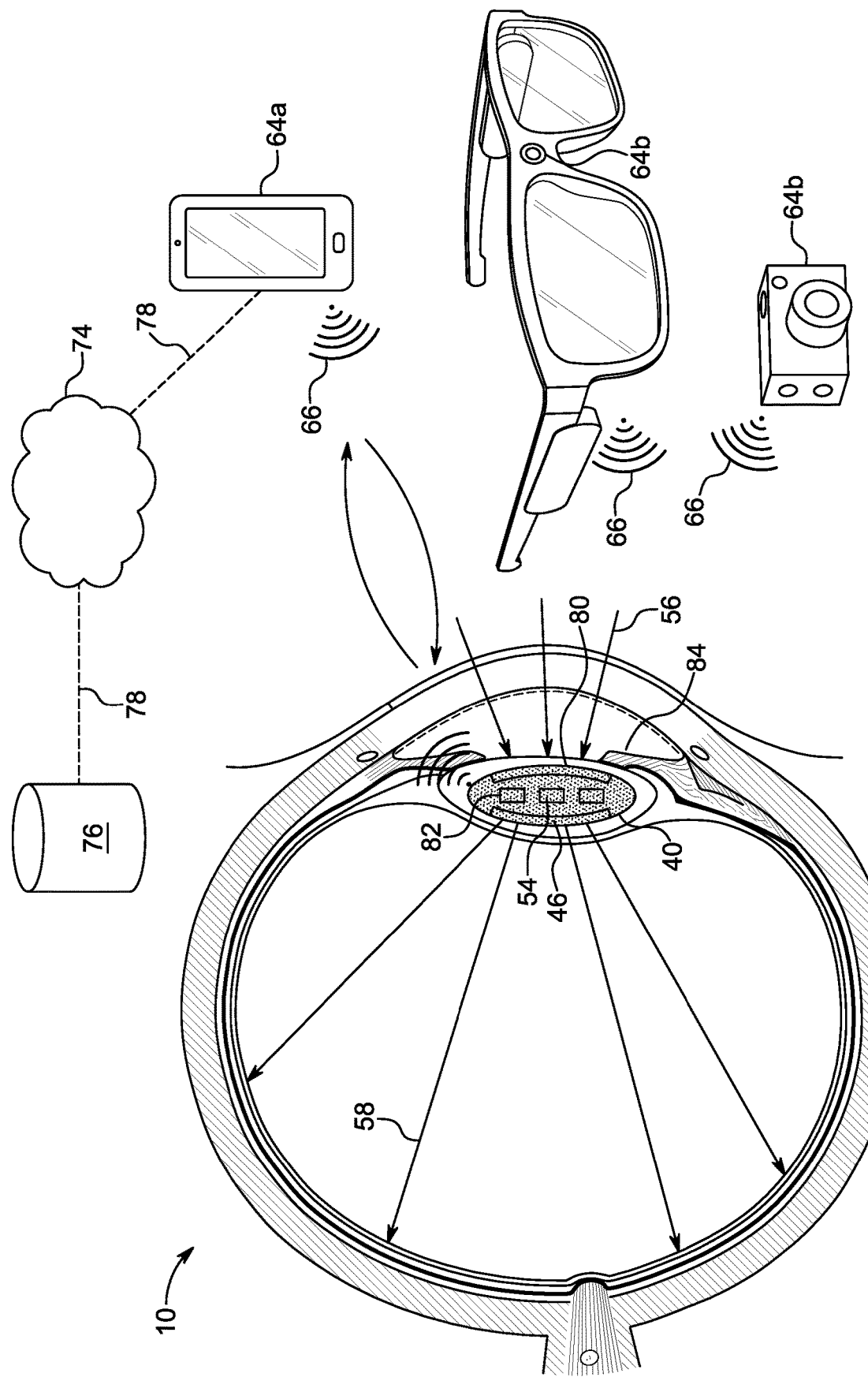
FIG. 17 is a view of an exemplary system having an intraocular implant device with a power harnessing digital camera, power supply, projector, wireless transceiver, and processor receiving and/or sending data to secondary devices.
Figure 18:
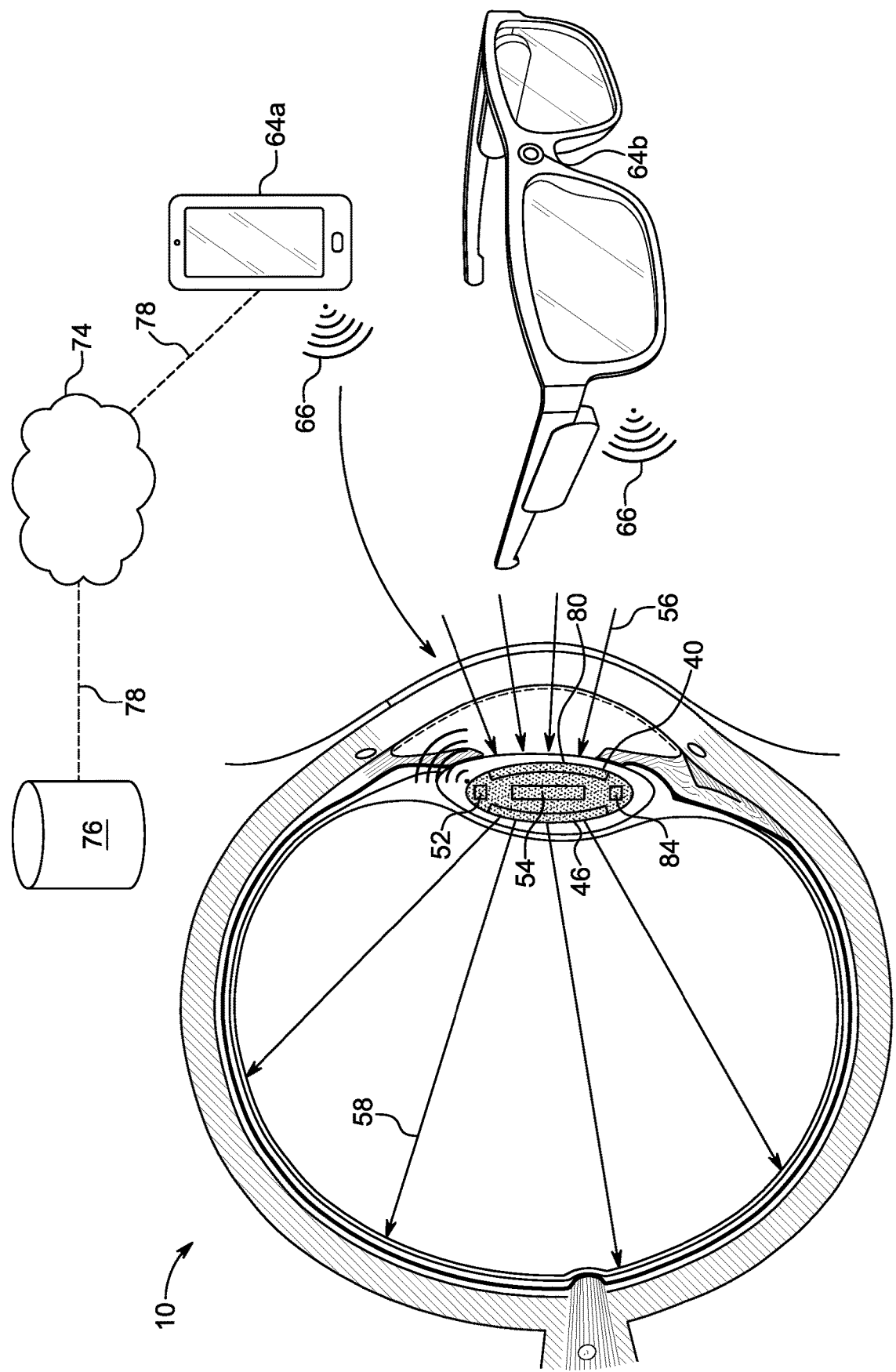
FIG. 18 is a view of an exemplary system having an intraocular implant device with a power harnessing digital camera, power supply, projector, wireless receiver, and processor receiving data from secondary devices.

Referring to FIGS. 13 and 14, other embodiments may provide the user with augmented reality. The intraocular device 40 may further comprise a wireless receiver and transmitter 82. In this embodiment, a first image received by the power harnessing digital camera 80 may be transmitted wirelessly to an extraocular device 64 such as a wireless device, a cellular device, a smart phone or another computing device that may process the first image. During processing, the wireless device or other computing device 64 may overlay a second image on top of the first image to form an augmented image. The wireless device or other computing device 64 may then transmit the augmented image back to the projector 46 via the wireless receiver 82. The augmented image is then transferred to the projector 46 which then projects the augmented image to the retina 14 of a user. This allows a user to experience an augmented reality by allowing the input to be altered and transmitted to the user.

Referring to FIGS. 15-18, another variation of the augmented reality embodiment of the intraocular device further comprises a processor 84. In this embodiment, the intraocular device 40 is capable of overlaying a second image onto the first image via the processor 84 all within the intraocular device 40, thus resulting in a faster processing of the image. Because the image is processed by the processor 84 directly in the intraocular device 40, another embodiment may remove the wireless transmission 82 function of the intraocular device 40 and may only contain a wireless receiver 52. This would reduce the energy demands on the intraocular device 40. The processor 40 is operable to overlay various sets of data onto digital data. For example, the processor 40 may take a first set of digital data including GPS data and overlay that data onto a video feed, thus forming an overlaid image.

Figure 19:
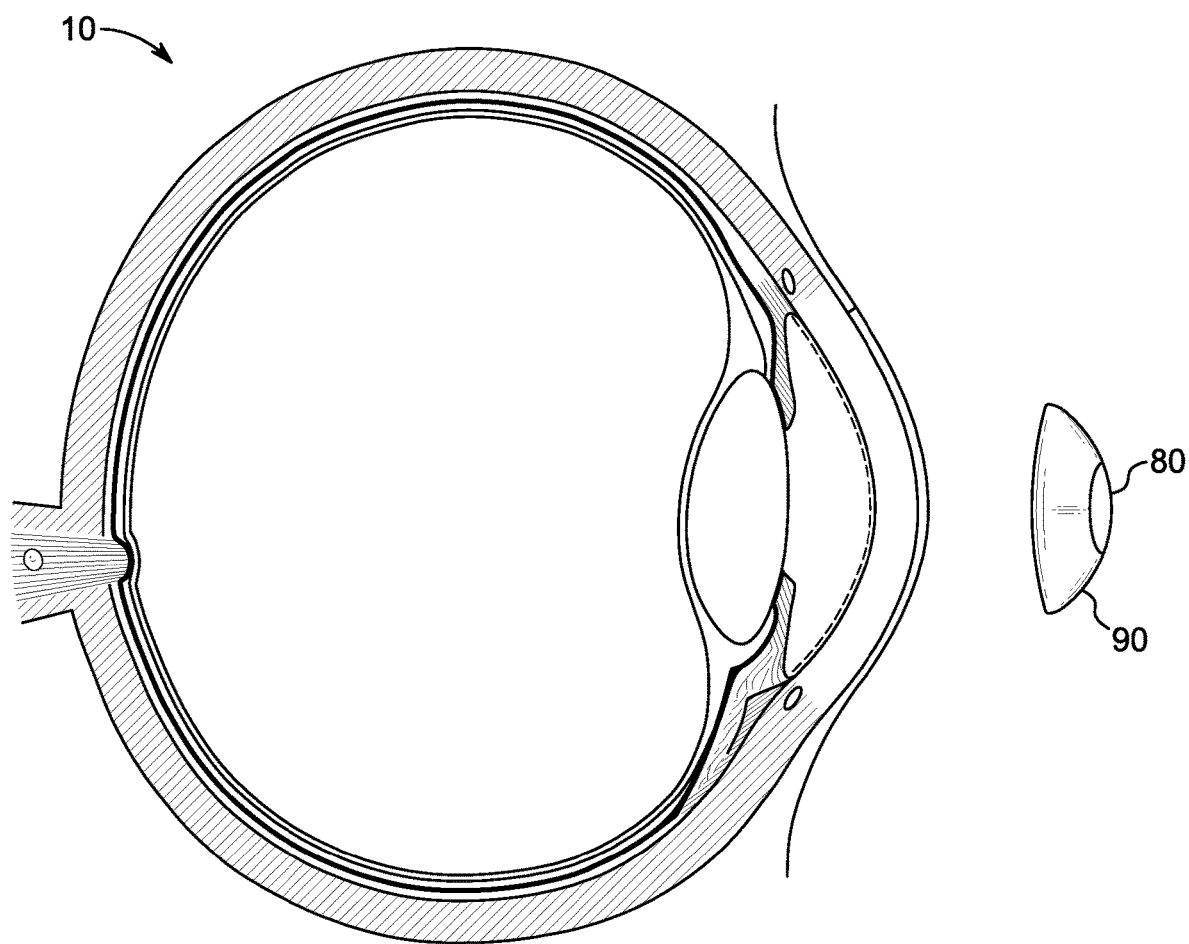
FIG. 19 is a schematic view of an extraocular lens.
Figure 20:
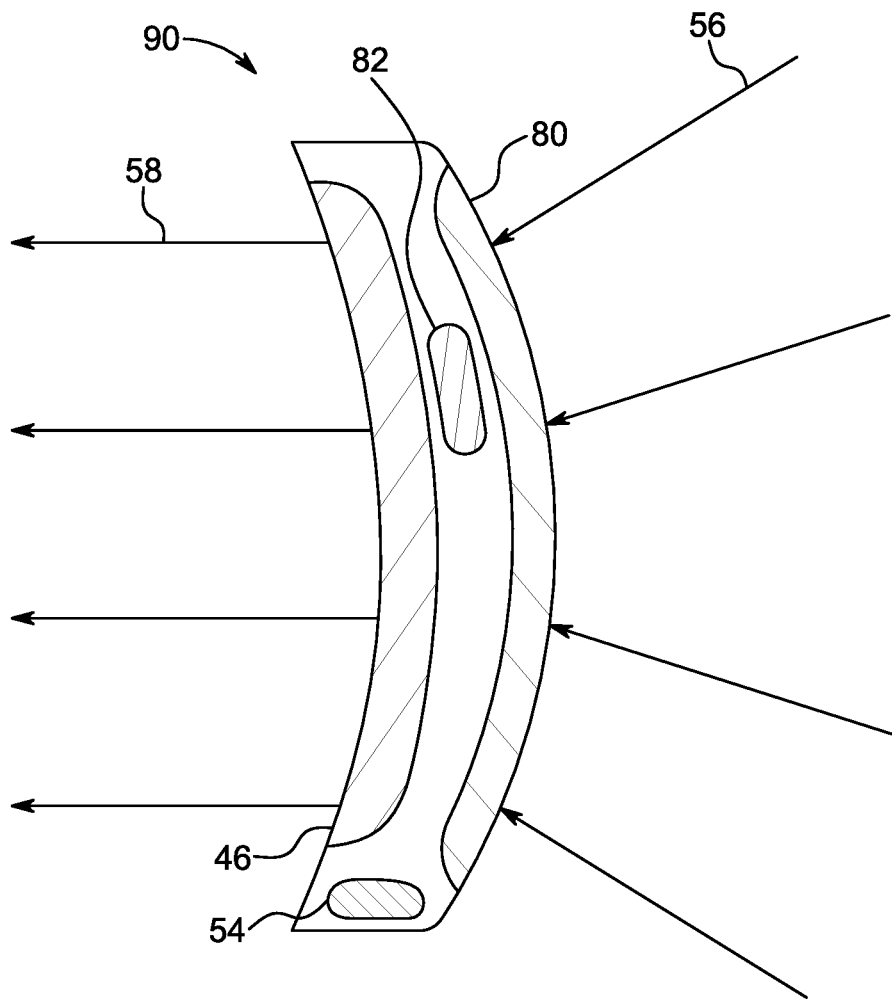
FIG. 20 is a schematic view of an extraocular lens having a power harnessing digital camera, a power supply, a projector, and a wireless receiver.
Figure 21:
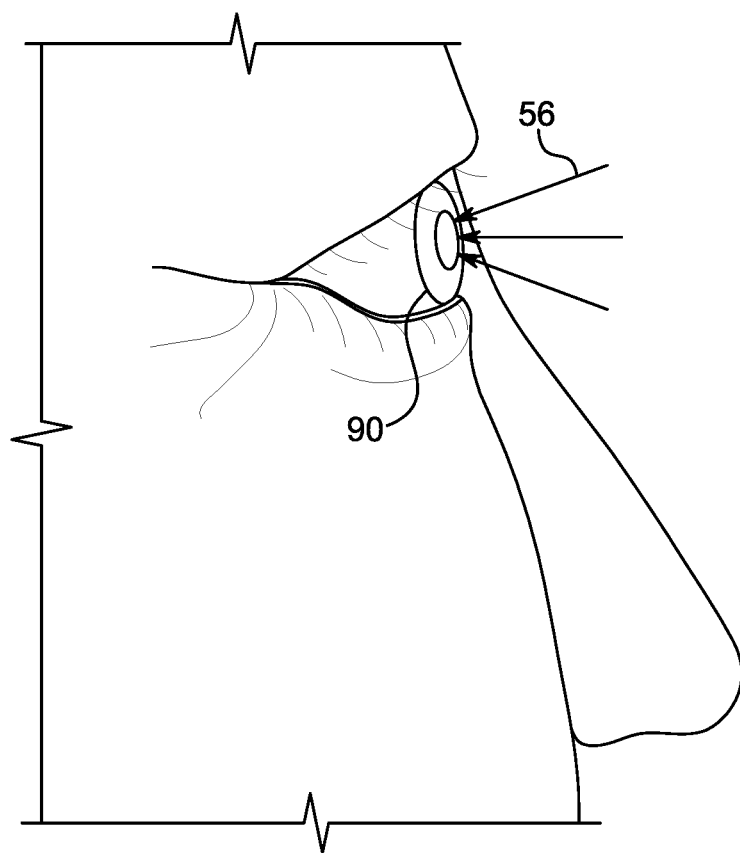
FIG. 21 is a schematic view of an extraocular lens positioned radially outward on the cornea of a user.

Referring to FIGS. 19-21, in other embodiments, the device 40 may be an extraocular device 90 comprising a power harnessing digital camera 80 or photoelectric array, a power supply 54, and a projector 46. The epicorneal, or extraocular device 90 can be worn like a contact lens, where the device rests radially outward on the cornea 12 of a user. The extraocular device 90 may also have a wireless transceiver 82 and processor 84 as previously discussed to provide an augmented reality experience for the user.

The augmented experience may include many functionalities such as overlaying information such as navigation applications, electronic mail messages, SMS messages, secondary video feeds, digital animations, etc.

In other embodiments, the intraocular and extraocular devices 40, 90 may provide an immersive experience. The projector 46 and wireless receiver 52 may be used to transmit images and data directly to the eye 10, thus effectively utilizing the user's eye 10 as the screen (Your-Eye-As-The-Screen or YEATScreen). Movies, videos, and other images may be transmitted from a wireless devices 64 to the wireless receiver 52, which then would transfer that data to the projector 46. The projector 46 would then project those images directly onto the retina 14 of the user. The device 40 may also be implanted in only one eye 10 of the user.

Figure 22:
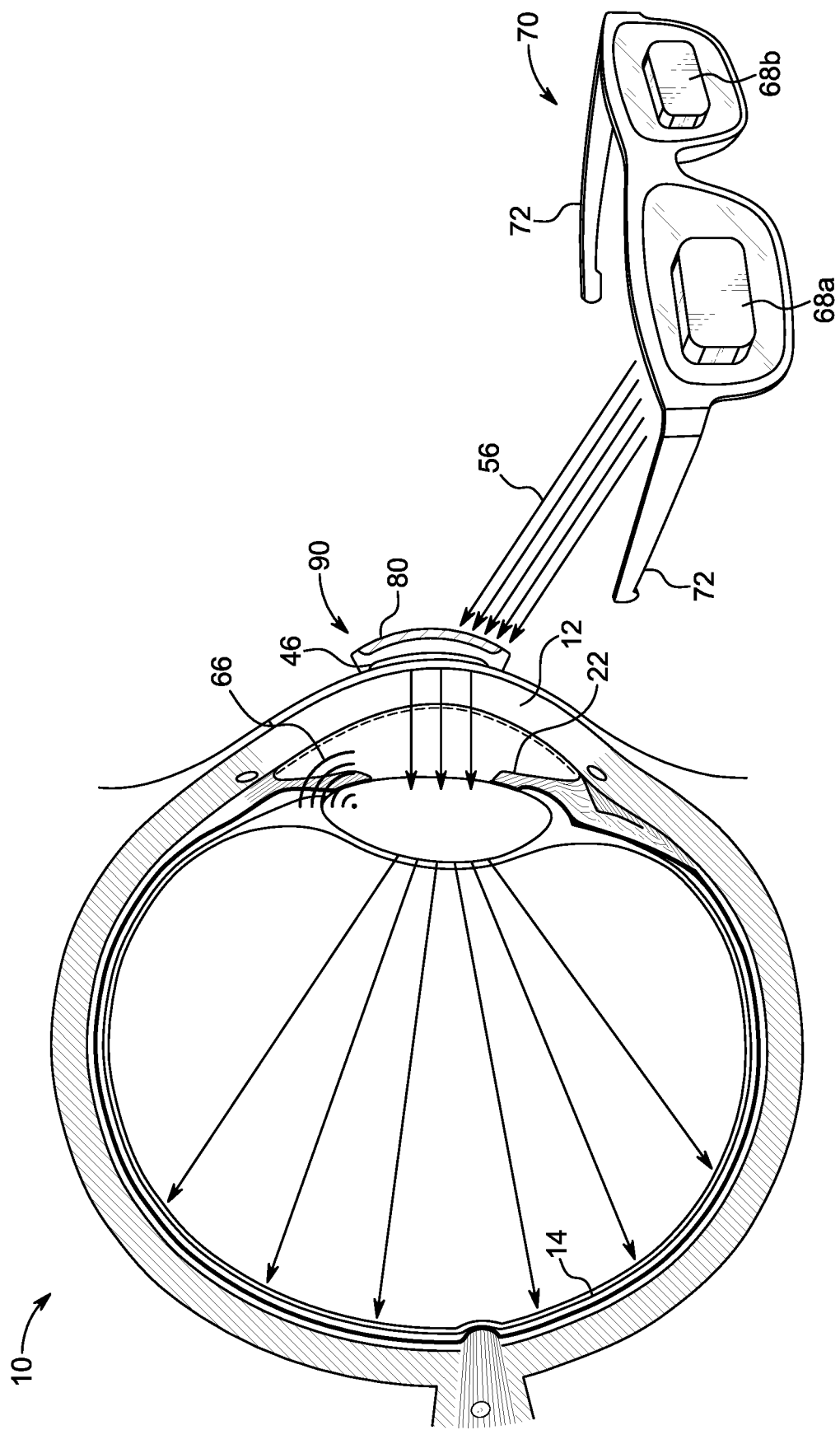
FIG. 22 is a schematic view of an embodiment of an extraocular lens positioned radially outward on the cornea of a user, and an external light source irradiating the extraocular lens.

FIG. 22 depicts an embodiment of an extraocular lens 90 positioned radially outward over the cornea 12 of a user. The extraocular lens 90 is receiving incident light 56 from a device 68a mounted radially outward from the extraocular lens 90 of the user. The incident light source 68a may be mounted on glasses 72 of a user. The incident light source 68a may be used to power the extraocular lens 90, especially when the extraocular lens 90 needs supplemental power because it is not able to receive and store enough power from natural incident light 56.

Thus, although there have been described particular embodiments of the present invention of a new and useful ARTIFICIAL VISION INTRAOCULAR IMPLANT DEVICE, it is not intended that such references to particular embodiments be construed as limitations upon the scope of this invention.

What is claimed is:

1. An intraocular implant device, comprising:
   an intraocular implant body shaped for positioning inside a lens chamber of an eye, the intraocular implant body having an anterior side for facing a cornea of the eye, and a posterior side for facing a retina of the eye;
   a photoelectric sensor disposed on the anterior side of the intraocular implant body, wherein the photoelectric sensor is operable to receive incident light through the cornea and to convert the incident light into electrical energy for use with one or more circuit components disposed on the intraocular implant body, and
   wherein the photoelectric sensor is also operable to convert the incident light into image data, and
   wherein the photoelectric sensor comprises a picture element operable to detect chrominance and luminance of the incident light and a photoelectric element disposed proximate the picture element.

2. The device of claim 1, further comprising:
   a light projector disposed on the posterior side of the intraocular implant body, the light projector configured to receive a digital input signal including the image data, and to emit photons from the light projector onto the retina in a pattern representative of the image data.

3. The device of claim 2, further comprising:
   an external light source spaced in relation to the intraocular implant body exterior to the eye, the external light source is operable to generate and emit the incident light through the cornea onto the photoelectric sensor disposed on the anterior side of the implant body.

4. The device of claim 1, wherein the photoelectric sensor further comprises a light filter proximate the picture element, wherein the light filter is configured to permit specific wavelengths of light to pass through to the picture element.

5. The device of claim 1, wherein the photoelectric sensor further comprises a prism disposed anterior the picture element, wherein the prism separates incident light according to wavelength.

6. An intraocular implant device, comprising:
   an intraocular implant body shaped for positioning inside a lens chamber of an eye, the intraocular implant body having an anterior side for facing a cornea of the eye, and a posterior side for facing a retina of the eye;
   a photoelectric sensor disposed on the anterior side of the intraocular implant body, wherein the photoelectric sensor is operable to receive incident light through the cornea and to convert the incident light into electrical energy for use with one or more circuit components disposed on the intraocular implant body, and
   wherein the photoelectric sensor is also operable to convert the incident light into image data, and
   wherein the photoelectric sensor comprises a plurality of stacked photoelectric p-n junctions, wherein each stacked photoelectric p-n junction is receptive to a specific bandwidth of light frequencies.

7. A method of providing artificial vision to a user, comprising:
   implanting an intraocular implant device into a lens chamber of a user, wherein the intraocular device comprises:
      an intraocular implant body,
      a photoelectric power harnessing camera disposed on the intraocular implant body, and
      a projector operable to receive power and an input signal from the photoelectric power harnessing camera, the input signal representing images;
   projecting the images represented in the input signal onto a retina of the user;
   transmitting the input signal from a wireless transceiver disposed in the intraocular implant device to an external device prior to projecting;
   modifying the input signal in the external device; and
   re-transmitting the input signal from the external device to the wireless transceiver.

8. The method of claim 7, further comprising transmitting a second input signal from an external device to a wireless receiver disposed in the intraocular implant device.

9. The method of claim 8, further comprising integrating the second input signal into the input signal via a processor disposed in the intraocular implant device prior to projecting the input signal.

10. The method of claim 9, wherein the second input signal includes a GPS overlay input signal.

11. The method of claim 7, further comprising supplying the intraocular implant device with optimized light power from a light emitting contact lens or a light emitting device mounted to glasses of a user.

* * * * *